(12) United States Patent
Saji et al.

(10) Patent No.: US 11,027,026 B2
(45) Date of Patent: Jun. 8, 2021

(54) POLYMER, AND CONTRAST AGENT FOR PHOTOACOUSTIC IMAGING, INCLUDING THE POLYMER

(71) Applicant: CANON KABUSHIKI KAISHA, Tokyo (JP)

(72) Inventors: Hideo Saji, Kyoto (JP); Kohei Sano, Kyoto (JP); Akira Makino, Kyoto (JP); Kengo Kanazaki, Yokohama (JP); Fumio Yamauchi, Yokohama (JP); Satoshi Ogawa, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 590 days.

(21) Appl. No.: 15/511,898

(22) PCT Filed: Oct. 16, 2015

(86) PCT No.: PCT/JP2015/079908
§ 371 (c)(1),
(2) Date: Mar. 16, 2017

(87) PCT Pub. No.: WO2016/060277
PCT Pub. Date: Apr. 21, 2016

(65) Prior Publication Data
US 2018/0228922 A1     Aug. 16, 2018

(30) Foreign Application Priority Data

Oct. 16, 2014  (JP) .................................. 2014-211915
Apr. 30, 2015  (JP) ............................ JP2015-092782

(51) Int. Cl.
*A61K 9/00*       (2006.01)
*A61K 49/00*      (2006.01)
(Continued)

(52) U.S. Cl.
CPC ...... *A61K 49/0034* (2013.01); *A61K 49/0054* (2013.01); *C08G 73/0233* (2013.01); *G01N 33/574* (2013.01)

(58) Field of Classification Search
CPC ................................................... A61K 49/0034
See application file for complete search history.

(56) References Cited

U.S. PATENT DOCUMENTS 7,994,228 B2    8/2011  Nagamura
9,138,492 B2    9/2015  Fukui et al.
(Continued)

FOREIGN PATENT DOCUMENTS

JP    2009-185261 A    8/2009
JP    2011-527727 A    11/2011
(Continued)

OTHER PUBLICATIONS

Machine translation of JP2014185312, Nov. 2019.*
(Continued)

*Primary Examiner* — Paul W Dickinson
(74) *Attorney, Agent, or Firm* — Venable LLP

(57) ABSTRACT

To provide a polymer having a high tumor/blood ratio. The present invention provides a polymer represented by the following formula (P1):

(Continued)

wherein in the formula (P1), $R_0$ represents any of a residue or a functional group derived from a cationic polymerization initiator; L represents a linker and L may not be present; n represents an integer of 1 or more; D represents a dye backbone of a dye having absorption in the near-infrared region.

14 Claims, 6 Drawing Sheets

(51) Int. Cl.
   *C08G 73/02* (2006.01)
   *G01N 33/574* (2006.01)

(56) References Cited

U.S. PATENT DOCUMENTS

| | | |
|---|---|---|
| 9,517,278 B2 | 12/2016 | Takahashi et al. |
| 9,592,307 B2 | 3/2017 | Yamauchi et al. |
| 10,398,788 B2 | 9/2019 | Kondo et al. |
| 2012/0114563 A1 | 5/2012 | Carter et al. |
| 2015/0290345 A1 | 10/2015 | Takahashi et al. |
| 2015/0374856 A1 | 12/2015 | Miki et al. |
| 2016/0279271 A1 | 9/2016 | Yamauchi et al. |
| 2018/0280547 A1 | 10/2018 | Saji et al. |

FOREIGN PATENT DOCUMENTS

| | | |
|---|---|---|
| JP | 2012-520856 A | 9/2012 |
| JP | 2014-185312 A | 10/2014 |
| WO | 2008/032818 A1 | 3/2008 |
| WO | 2010/006282 A2 | 1/2010 |
| WO | 2010/106169 A1 | 9/2010 |
| WO | 2013/103297 A1 | 7/2013 |
| WO | 2016/063817 A1 | 4/2016 |
| WO | 2017/057653 A1 | 4/2017 |

OTHER PUBLICATIONS

Kondo et al., U.S. Appl. No. 15/513,035, filed Mar. 21, 2017.
Notification of Reasons for Refusal in Japanese Application No. 2015-205024 (dated Sep. 19, 2019).
Saji et al., U.S. Appl. No. 15/762,251, filed Mar. 23, 2018.
Juliane Ulbricht et al. "On the Biodegradability of Polyethylene Glycol, Polypeptoids and Poly(2-oxazoline)s," 35(17) Biomaterials 4848-4861 (Mar. 2014) (XP055241156).
Kanyi Pu et al., "Semiconducting Polymer Nanoparticles as Photoacoustic Molecular Imaging Probes in Living Mice," 9 Nature Nanotechnology 233-239 (Jan. 2014) (XP055241143).
Tune B. Bonné et al., "Aggregation Behavior of Amphiphilic Poly(2-alkyl-2-oxazoline) Diblock Copolymers in Aqueous Solution Studied by Fluorescence Correlation Spectroscopy," 282(8) Colloid Polym. Sci. 833-843 (May 2004) (XP055240664).
Sonia Cesana et al., "First Poly(2-oxazoline)s with Pendant Amino Groups," 207 Macromol. Chem. Phys. 183-192 (2006) (XP008138009).
Tacey X. Viegas et al., "Polyoxazoline: Chemistry, Properties, and Applications in Drug Delivery," 22(5) Bioconjugate Chem. 976-986 (Apr. 2011) (XP55082338).

\* cited by examiner

POLYMER, AND CONTRAST AGENT FOR PHOTOACOUSTIC IMAGING, INCLUDING THE POLYMER

TECHNICAL FIELD

The present invention relates to a polymer, and a contrast agent for photoacoustic imaging, including the polymer.

BACKGROUND ART

A photoacoustic tomography (hereinafter, sometimes abbreviated as "PAT") apparatus is known as one apparatus for visualizing information in a living body. In measurement using the PAT apparatus, an image in which the substance distribution in an object to be measured is computed can be obtained by measuring the intensity and the time of generation of a photoacoustic signal emitted from a substance (optical absorber) that absorbs light in the object to be measured, in irradiation of the object to be measured with light.

For the optical absorber, any substance can be here used as long as the substance absorbs light and emits an acoustic wave in a living body. For example, a blood vessel or a malignant tumor in a human body can be adopted for the optical absorber. Besides, molecules of indocyanine green (hereinafter, sometimes abbreviated as "ICG") and the like can also be administered into a body and utilized as a contrast agent. ICG well absorbs light in the near-infrared wavelength region, the light having a small influence in irradiation of a human body therewith and having a high permeability to a living body, and therefore can be suitably used as a contrast agent (sometimes abbreviated as a "photoacoustic contrast agent") in the PAT apparatus. In the present description, ICG refers to a compound represented by a structure of the following formula.

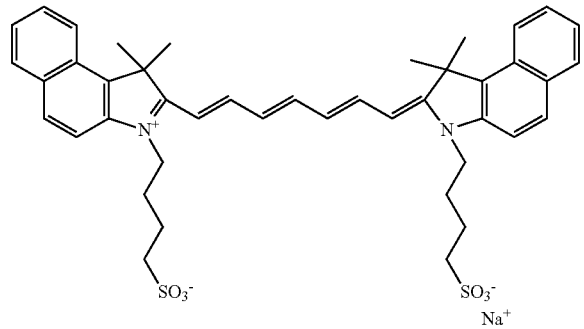

Herein, the counter ion may not be $Na^+$, and any counter ion such as $H^+$ or $K^+$ can be used.

It is known that, however, ICG has a very short half-life of about several minutes in blood.

PTL 1 reports an example in which a tumor accumulation is confirmed using a contrast agent in which polyethylene glycol (hereinafter, sometimes abbreviated as "PEG") is covalently bound to a near-infrared dye. The near-infrared dye can be bound to PEG to thereby allow the half-life in blood to be prolonged as compared with a single near-infrared dye.

CITATION LIST

Patent Literature

PTL 1: Japanese Patent Application Laid-Open No. 2012-520856

Non Patent Literature

NPL 1: Biomaterials, (2014), 35(17), 4848-4861

SUMMARY OF INVENTION

Technical Problem

While the near-infrared fluorescent dye-bound PEG disclosed in PTL 1 exhibits a high tumor accumulation property, the dye-bound PEG has a high retentivity in blood, and therefore has the problem of being low in tumor/blood ratio.

Then, an object of the present invention is to provide a polymer having a high tumor/blood ratio, and a contrast agent for photoacoustic imaging, including the polymer.

Solution to Problem

The present invention provides a polymer represented by the following formula (P1).

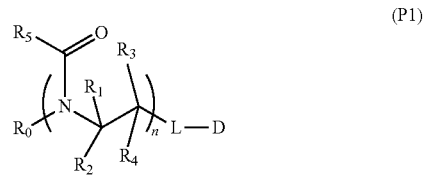

In the formula (P1), $R_0$ represents any of a residue derived from a cationic polymerization initiator, or a functional group; L represents a linker and L may not be present; n represents an integer of 1 or more; D represents a dye backbone of a dye having absorption in the near-infrared region; $R_1$ to $R_4$ each independently represent a hydrogen atom, or a substituted or unsubstituted hydrocarbon group having 1 or more and 4 or less carbon atoms, in which, when a substituent is present, the substituent is a functional group including at least one selected from the group consisting of a halogen atom, an oxygen atom and a nitrogen atom; and $R_5$ represents any of a methyl group, an ethyl group, an isopropyl group, a n-propyl group, a n-butyl group, a n-octyl group, a n-heptyl group, a phenyl group, a butenyl group and a pentynyl group.

One example of D in the formula (P1) of the polymer according to the present embodiment can include one represented by the following formula (d1) or (d2).

(d1)

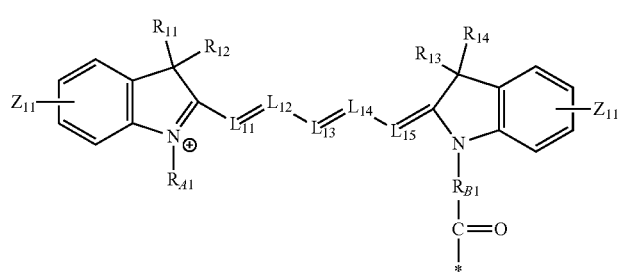

(d2)

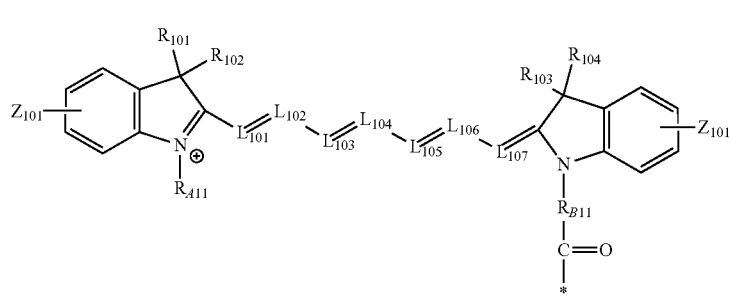

In the formula (d1), $L_{11}$, $L_{12}$, $L_{13}$, $L_{14}$ and $L_{15}$ may be each the same or different, and represent CH or $CR_{15}$, and $R_{15}$ represents a straight or branched alkyl group having 1 to 10 carbon atoms. $L_{11}$, $L_{12}$, $L_{13}$, $L_{14}$ and $L_{15}$ may be bound together to form a 4-membered ring to a 6-membered ring. $R_{11}$, $R_{12}$, $R_{13}$ and $R_{14}$ may be each the same or different, and represent a hydrogen atom, a straight or branched alkyl group having 1 to 10 carbon atoms, $-R_{D1}-SO_3^-$, or $-R_{E1}-SO_3X_{11}$. $R_{D1}$ and $R_{E1}$ represent a straight or branched alkylene group having 1 to 10 carbon atoms. $X_{11}$ represents any of a hydrogen atom, a sodium atom, a potassium atom, or a cation derived from ammonia, triethylamine, lysine or arginine. $R_{A1}$ represents a straight or branched alkyl group having 1 to 10 carbon atoms, $-R_{C1}-SO_3^-$, $-R_{G1}-SO_3X_{15}$, or $-R_{F1}-CO_2X_{14}$. $X_{14}$ and $X_{15}$ represent any of a hydrogen atom, a sodium atom, a potassium atom, or a cation derived from ammonia, triethylamine, lysine or arginine. $R_{C1}$, $R_{F1}$ and $R_{G1}$ represent a straight or branched alkylene group having 1 to 10 carbon atoms. When $R_{A1}$ represents a straight or branched alkyl group having 1 to 10 carbon atoms, a halogen ion or an organic acid ion may be included as a counter ion. $R_{B1}$ represents a straight or branched alkylene group having 1 to 10 carbon atoms. $Z_{11}$ mutually independently represents a hydrogen atom or $-SO_3X_{12}$, or may be taken together with an indole ring bound to $Z_{11}$ to form a cyclic aromatic ring including a benz[e]indole ring, a benz[f]indole ring or a benz[g]indole ring, and furthermore, a hydrogen atom in the cyclic aromatic ring may be substituted with a straight or branched alkyl group having 1 to 10 carbon atoms, a straight or branched alkoxy group having 1 to 10 carbon atoms, or $-SO_3X_{13}$. $X_{12}$ and $X_{13}$ represent any of a hydrogen atom, a sodium atom, a potassium atom, or a cation derived from ammonia, triethylamine, lysine or arginine, and * represents binding to L, or represents binding to the carbon atom at the terminal of the repeating unit in the formula (P1) when the polymer does not include L.

In the formula (d2), $L_{101}$, $L_{102}$, $L_{103}$, $L_{104}$, $L_{105}$, $L_{106}$ and $L_{107}$ may be each the same or different, and represent CH or $CR_{105}$, and $R_{105}$ represents a straight or branched alkyl group having 1 to 10 carbon atoms. $L_{101}$, $L_{102}$, $L_{103}$, $L_{104}$, $L_{105}$, $L_{106}$ and $L_{107}$ may be bound together to form a 4-membered ring to a 6-membered ring. $R_{101}$, $R_{102}$, $R_{103}$ and $R_{104}$ may be each the same or different, and represent a hydrogen atom, a straight or branched alkyl group having 1 to 10 carbon atoms, $-R_{D11}-SO_3^-$, or $-R_{E11}-SO_3X_{101}$. $R_{D11}$ and $R_{E11}$ represent a straight or branched alkylene group having 1 to 10 carbon atoms. $X_{101}$ represents any of a hydrogen atom, a sodium atom, a potassium atom, or a cation derived from ammonia, triethylamine, lysine or arginine. $R_{A11}$ represents a straight or branched alkyl group having 1 to 10 carbon atoms, $-R_{C11}-SO_3^-$, $-R_{G11}-SO_3X_{105}$, or $-R_{F11}-CO_2X_{104}$. $X_{104}$ and $X_{105}$ represent any of a hydrogen atom, a sodium atom, a potassium atom, or a cation derived from ammonia, triethylamine, lysine or arginine. $R_{C11}$, $R_{F11}$ and $R_{G11}$ represent a straight or branched alkylene group having 1 to 10 carbon atoms. When $R_{A11}$ represents a straight or branched alkyl group having 1 to 10 carbon atoms, a halogen ion or an organic acid ion may be included as a counter ion. $R_{B11}$ represents a straight or branched alkylene group having 1 to 10 carbon atoms. $Z_{101}$ mutually independently represents a hydrogen atom or $-SO_3X_{102}$, or is taken together with an indole ring bound to $Z_{101}$ to form a cyclic aromatic ring including a benz[e]indole ring, a benz[f]indole ring or a benz[g]indole ring, and a hydrogen atom in the cyclic aromatic ring may be substituted with a straight or branched alkyl group having 1 to 10 carbon atoms, a straight or branched alkoxy group having 1 to 10 carbon atoms, or $-SO_3X_{103}$. $X_{102}$ and $X_{103}$ represent any of a hydrogen atom, a sodium atom, a potassium atom, or a cation derived from ammonia, triethylamine, lysine or arginine, and * represents binding to L, or represents binding to the carbon atom at the terminal of the repeating unit in the formula (P1) when the polymer does not include L.

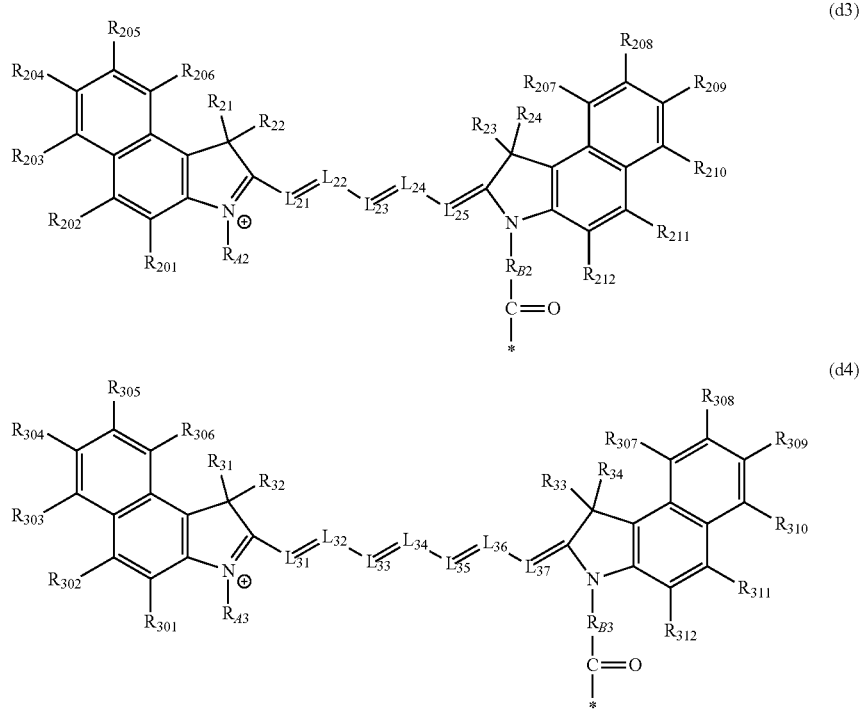

Furthermore, the formulae (d1) and (d2) can also be represented by the formulae (d3) and (d4), respectively. In the formula (d3), $R_{201}$ to $R_{212}$ may be each the same or different, and represent a hydrogen atom, a straight or branched alkyl group having 1 to 10 carbon atoms, or —$SO_3X_{24}$. $X_{24}$ represents any of a hydrogen atom, a sodium atom, a potassium atom, or a cation derived from ammonia, triethylamine, lysine or arginine. $L_{21}$, $L_{22}$, $L_{23}$, $L_{24}$ and $L_{25}$ may be each the same or different, and represent CH or $CR_{25}$, and $R_{25}$ represents a straight or branched alkyl group having 1 to 10 carbon atoms. $L_{21}$, $L_{22}$, $L_{23}$, $L_{24}$ and $L_{25}$ may be bound together to form a 4-membered ring to a 6-membered ring. $R_{21}$, $R_{22}$, $R_{23}$ and $R_{24}$ may be each the same or different, and represent a hydrogen atom, a straight or branched alkyl group having 1 to 10 carbon atoms, —$R_{D2}$—$SO_3^-$, or —$R_{E2}$—$SO_3X_{21}$. $R_{D2}$ and $R_{E2}$ represent a straight or branched alkylene group having 1 to 10 carbon atoms. $X_{21}$ represents any of a hydrogen atom, a sodium atom, a potassium atom, or a cation derived from ammonia, triethylamine, lysine or arginine. $R_{42}$ represents a straight or branched alkyl group having 1 to 10 carbon atoms, —$R_{C2}$—$SO_3^-$, —$R_{G2}$—$SO_3X_{25}$, or —$R_{F2}$—$CO_2X_{26}$. $X_{25}$ and $X_{26}$ represent any of a hydrogen atom, a sodium atom, a potassium atom, or a cation derived from ammonia, triethylamine, lysine or arginine. $R_{C2}$, $R_{F2}$ and $R_{G2}$ represent a straight or branched alkylene group having 1 to 10 carbon atoms. When $R_{42}$ represents a straight or branched alkyl group having 1 to 10 carbon atoms, a halogen ion such as a chloride ion, a bromide ion or an iodide ion, or an organic acid ion such as an acetate ion, a tartrate ion or a succinate ion may be included as a counter ion. $R_{B2}$ represents a straight or branched alkylene group having 1 to 10 carbon atoms. * represents binding to L, or represents binding to the carbon atom at the terminal of the repeating unit in the formula (P1) when the polymer does not include L. In the formula (d4), $R_{301}$ to $R_{312}$ may be each the same or different, and represent a hydrogen atom, a straight or branched alkyl group having 1 to 10 carbon atoms, or —$SO_3X_{34}$. $X_{34}$ represents any of a hydrogen atom, a sodium atom, a potassium atom, or a cation derived from ammonia, triethylamine, lysine or arginine. $L_{31}$, $L_{32}$, $L_{33}$, $L_{34}$, $L_{35}$, $L_{36}$ and $L_{37}$ may be each the same or different, and represent CH or $CR_{35}$, and $R_{35}$ represents a straight or branched alkyl group having 1 to 10 carbon atoms. $L_{31}$, $L_{32}$, $L_{33}$, $L_{34}$, $L_{35}$, $L_{36}$ and $L_{37}$ may be bound together to form a 4-membered ring to a 6-membered ring. $R_{31}$, $R_{32}$, $R_{33}$ and $R_{34}$ may be each the same or different, and represent a hydrogen atom, a straight or branched alkyl group having 1 to 10 carbon atoms, —$R_{D3}$—$SO_3^-$, or —$R_{E3}$—$SO_3X_{31}$. $R_{D3}$ and $R_{E3}$ represent a straight or branched alkylene group having 1 to 10 carbon atoms. $X_{31}$ represents any of a hydrogen atom, a sodium atom, a potassium atom, or a cation derived from ammonia, triethylamine, lysine or arginine. $R_{43}$ represents a straight or branched alkyl group having 1 to 10 carbon atoms, —$R_{C3}$—$SO_3^-$, —$R_{G3}$—$SO_3X_{35}$, or —$R_{F3}$—$CO_2X_{36}$. $X_3$ and $X_{36}$ represent any of a hydrogen atom, a sodium atom, a potassium atom, or a cation derived from ammonia, triethylamine, lysine or arginine. $R_{C3}$, $R_{F3}$ and $R_{G3}$ represent a straight or branched alkylene group having 1 to 10 carbon atoms. When $R_{43}$ represents a straight or branched alkyl group having 1 to 10 carbon atoms, a halogen ion such as a chloride ion, a bromide ion or an iodide ion, or an organic acid ion such as an acetate ion, a tartrate ion or a succinate ion may be included as a counter ion. $R_{B3}$ represents a straight or branched alkylene group having 1 to 10 carbon atoms. * represents binding to L, or represents binding to the carbon atom at the terminal of the repeating unit in the formula (P1) when the polymer does not include L.

Advantageous Effects of Invention

The polymer according to the present invention, the main chain of which has a structure of polyoxazoline or an analog thereof, is thus accumulated in a tumor, and excreted from blood with the lapse of time, and therefore can be used for a contrast agent that has a high tumor/blood ratio and that enable us to detect a tumor selectively.

Further features of the present invention will become apparent from the following description of exemplary embodiments with reference to the attached drawings.

BRIEF DESCRIPTION OF DRAWINGS

FIGS. 5A, 5B and 5C represent the case of $^{111}$In-labeled DOTA-P19, the case of $^{111}$In-labeled DOTA-P18 and the case of $^{111}$In-labeled DOTA-P13, respectively.

FIG. 7A illustrates a time-dependent change in the concentration in blood, and FIG. 7B illustrates a plot of the molecular weights of the polymers against half-time in blood.

DESCRIPTION OF EMBODIMENTS

Figure 1:
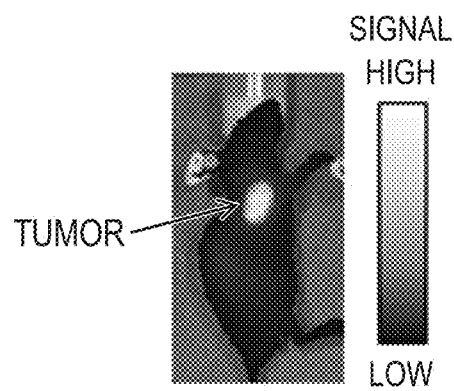
FIG. 1 illustrates a whole-body fluorescence image of a tumor-bearing mouse at 24 hours after administration of polymer P6 in Example of the present invention.

Preferred embodiments of the present invention will now be described in detail in accordance with the accompanying drawings.

A polymer according to an embodiment of the present invention is described, but the present invention is not limited thereto.

The polymer according to the present embodiment has a structure in which polyoxazoline or an analog thereof serves as a main chain and a near-infrared dye is bound to the polymer terminal. Specifically, the polymer has a structure represented by the following formula (P1).

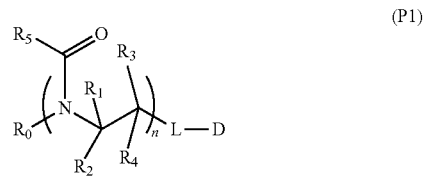

(P1)

In the formula (P1), $R_0$ is not particularly limited, and represents any of a residue derived from a cationic polymerization initiator, and a functional group. In the formula (P1), L represents a linker and L may not be present; n represents an integer of 1 or more; D represents a dye backbone of a dye having absorption in the near-infrared region; $R_1$ to $R_4$ each independently represent a hydrogen atom, or a substituted or unsubstituted hydrocarbon group having 1 or more and 4 or less carbon atoms, in which, when a substituent is present, the substituent is a functional group including at least one selected from the group consisting of a halogen atom, an oxygen atom and a nitrogen atom; and $R_5$ represents any of a methyl group, an ethyl group, an isopropyl group, a n-propyl group, a n-butyl group, a n-octyl group, a n-heptyl group, a phenyl group, a butenyl group and a pentynyl group. One example of D in the formula (P1) of the polymer according to the present embodiment can include one represented by the following formula (d1) or (d2).

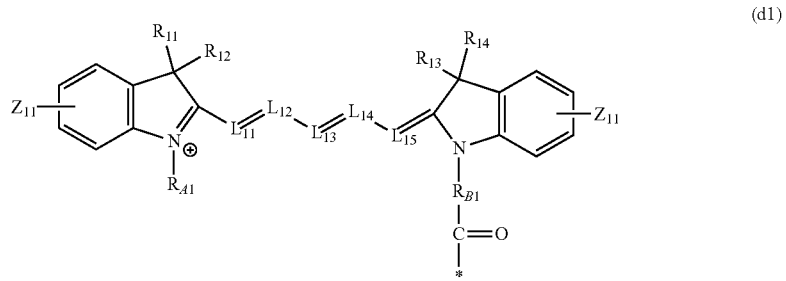

(d1)

(d2)

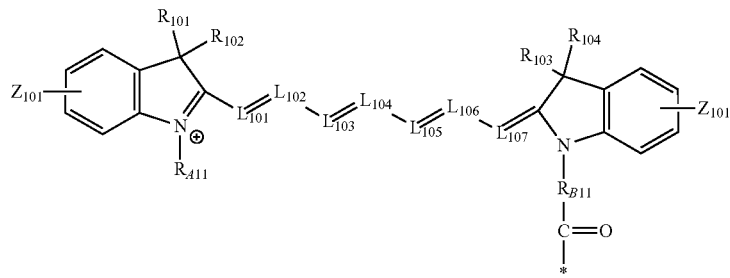

In the formula (d1), $L_{11}$, $L_{12}$, $L_{13}$, $L_{14}$ and $L_{15}$ may be each the same or different, and represent CH or $CR_{15}$, and $R_{15}$ represents a straight or branched alkyl group having 1 to 10 carbon atoms. $L_{11}$, $L_{12}$, $L_{13}$, $L_{14}$ and $L_{15}$ may be bound together to form a 4-membered ring to a 6-membered ring. $R_{11}$, $R_{12}$, $R_{13}$ and $R_{14}$ may be each the same or different, and represent a hydrogen atom, a straight or branched alkyl group having 1 to 10 carbon atoms, $-R_{D1}-SO_3^-$, or $-R_{E1}-SO_3X_{11}$. $R_{D1}$ and $R_{E1}$ represent a straight or branched alkylene group having 1 to 10 carbon atoms. $X_{11}$ represents any of a hydrogen atom, a sodium atom, a potassium atom, or a cation derived from ammonia, triethylamine, lysine or arginine. $R_{41}$ represents a straight or branched alkyl group having 1 to 10 carbon atoms, $-R_{C1}-SO_3^-$, $-R_{G1}-SO_3X_{15}$, or $-R_{F1}-CO_2X_{14}$. $X_{14}$ and $X_{15}$ represent any of a hydrogen atom, a sodium atom, a potassium atom, or a cation derived from ammonia, triethylamine, lysine or arginine. $R_{C1}$, $R_{F1}$ and $R_{G1}$ represent a straight or branched alkylene group having 1 to 10 carbon atoms. When $R_{41}$ represents a straight or branched alkyl group having 1 to 10 carbon atoms, a halogen ion or an organic acid ion may be included as a counter ion. $R_{B1}$ represents a straight or branched alkylene group having 1 to 10 carbon atoms. $Z_{11}$ mutually independently represents a hydrogen atom or $-SO_3X_{12}$, or may be taken together with an indole ring bound to $Z_{11}$ to form a cyclic aromatic ring including a benz[e]indole ring, a benz[f]indole ring or a benz[g]indole ring, and furthermore, a hydrogen atom in the cyclic aromatic ring may be substituted with a straight or branched alkyl group having 1 to 10 carbon atoms, a straight or branched alkoxy group having 1 to 10 carbon atoms, or $-SO_3X_{13}$. $X_{12}$ and $X_{13}$ represent any of a hydrogen atom, a sodium atom, a potassium atom, or a cation derived from ammonia, triethylamine, lysine or arginine, and * represents binding to L, or represents binding to the carbon atom at the terminal of the repeating unit in the formula (P1) when the polymer does not include L.

In the formula (d2), $L_{101}$, $L_{102}$, $L_{103}$, $L_{104}$, $L_{105}$, $L_{106}$ and $L_{107}$ may be each the same or different, and represent CH or $CR_{105}$, and $R_{105}$ represents a straight or branched alkyl group having 1 to 10 carbon atoms. $L_{101}$, $L_{102}$, $L_{103}$, $L_{104}$, $L_{105}$, $L_{106}$ and $L_{107}$ may be bound together to form a 4-membered ring to a 6-membered ring. $R_{101}$, $R_{102}$, $R_{103}$ and $R_{104}$ may be each the same or different, and represent a hydrogen atom, a straight or branched alkyl group having 1 to 10 carbon atoms, $-R_{D11}-SO_3^-$, or $-R_{E11}-SO_3X_{101}$. $R_{D11}$ and $R_{E11}$ represent a straight or branched alkylene group having 1 to 10 carbon atoms. $X_{101}$ represents any of a hydrogen atom, a sodium atom, a potassium atom, or a cation derived from ammonia, triethylamine, lysine or arginine. $R_{411}$ represents a straight or branched alkyl group having 1 to 10 carbon atoms, $-R_{C11}-SO_3^-$, $-R_{G11}-SO_3X_{105}$, or $-R_{F11}-CO_2X_{104}$. $X_{104}$ and $X_{105}$ represent any of a hydrogen atom, a sodium atom, a potassium atom, or a cation derived from ammonia, triethylamine, lysine or arginine. $R_{C11}$, $R_{F11}$ and $R_{G11}$ represent a straight or branched alkylene group having 1 to 10 carbon atoms. When $R_{411}$ represents a straight or branched alkyl group having 1 to 10 carbon atoms, a halogen ion or an organic acid ion may be included as a counter ion. $R_{B11}$ represents a straight or branched alkylene group having 1 to 10 carbon atoms. $Z_{101}$ mutually independently represents a hydrogen atom or $-SO_3X_{102}$, or is taken together with an indole ring bound to $Z_{101}$ to form a cyclic aromatic ring including a benz[e]indole ring, a benz[f]indole ring or a benz[g]indole ring, and a hydrogen atom in the cyclic aromatic ring may be substituted with a straight or branched alkyl group having 1 to 10 carbon atoms, a straight or branched alkoxy group having 1 to 10 carbon atoms, or $-SO_3X_{103}$. $X_{102}$ and $X_{103}$ represent any of a hydrogen atom, a sodium atom, a potassium atom, or a cation derived from ammonia, triethylamine, lysine or arginine, and * represents binding to L, or represents binding to the carbon atom at the terminal of the repeating unit in the formula (P1) when the polymer does not include L.

$R_0$ represents any of a residue derived from a cationic polymerization initiator, or a functional group, as described above. The functional group here includes, in addition to all general functional groups, groups derived from a low-molecular compound, a dye, a reporter molecule, a target-binding molecule, a polymer and the like. The groups derived from a low-molecular compound, a dye, a reporter molecule, a target-binding molecule, a polymer and the like include such a group that is bound via the residue derived from a cationic polymerization initiator, or $R_0$ that is substituted with a low-molecular compound, a dye, a reporter molecule, a target-binding molecule or a polymer as it is. With respect to the low-molecular compound, the dye, the reporter molecule, the target-binding molecule, the polymer and the like, a part of atoms included therein may be substituted with other atom in the course of binding. The functional group as $R_0$ in the polymer according to the present embodiment includes any groups, and one example thereof can include an alkyl group, a hydroxyl group, a carboxyl group, an amino group, a thiol group, an azido group, a diamine, a succinimidyl ester group, a maleimide group and a succinimide group. Examples of a compound as $R_0$ can include a low-molecular compound, a reporter molecule, a target-binding molecule and other polymer. Examples of the low-molecular compound include an inhibitor such as gefitinib. Examples of the reporter molecule include a molecule generating a physical signal such as a radioactive signal, a magnetic field signal, an ultrasonic signal, a fluorescent signal or an optical ultrasonic signal, and radioactive halogen, radioisotope, a paramagnetic metal ion, an iron oxide particle, a gold nanoparticle, a microbubble, a dye and an anticancer agent that are therapeutic agents. Examples of the dye include a fluorescent compound, a phosphorescent compound and a near-infrared light absorbing compound. Examples of the target-binding molecule include an antibody, an antibody fragment and artificial antibodies such as a single-strand antibody, and an enzyme, bioactive peptide, glycopeptide, a sugar chain, a lipid and a molecule-recognizing compound. Examples of other polymer as $R_0$ include polyethylene glycol, and such a polymer may have any degree of polymerization and may also be ethylene glycol.

The reason why the polymer according to the present embodiment shows high tumor/blood ratio is described. As an example, a case is described in which the polymer has polyoxazoline (hereinafter, sometimes abbreviated as "POZ") as a main chain of the formula (P1) and ICG as a near-infrared dye represented by D. The surface energy of each of POZ and ICG is evaluated, and a tendency is expected in which ICG and POZ are low in compatibility with each other and ICG is not covered with POZ.

On the other hand, with respect to ICG-bound PEG in the prior art, ICG and PEG are high in compatibility with each other and ICG is effectively covered with PEG. In the present embodiment, it is considered that, since ICG bound to POZ is not covered with POZ due to the above reason, the dye, protein in blood, and the like are brought into stochastic contact with each other, recognized as foreign substances, and delivered to the liver and the spleen, thereby allowing the effect of reducing the concentration in blood to be exerted.

POZ has been reported to be easily subjected to oxidative degradation as compared with PEG (NPL 1). Therefore, a probe retained in blood is metabolized and excreted by oxidative degradation with the lapse of time, and thus the concentration in blood decreases. As a result, it is considered that the effect of increasing the tumor/blood ratio is exerted. On the other hand, ICG-bound PEG in the prior art is not degraded but retained in blood for a long period, and thus the tumor/blood ratio is low.

Hereinafter, oxazoline as a monomer of polyoxazoline may be abbreviated as "OZ".

Examples of the formula (P1) include a polymer represented by the following formula (p1-1).

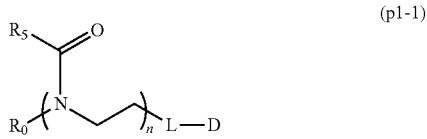

Examples of D above include the following formulae (d1-1) to (d1-6).

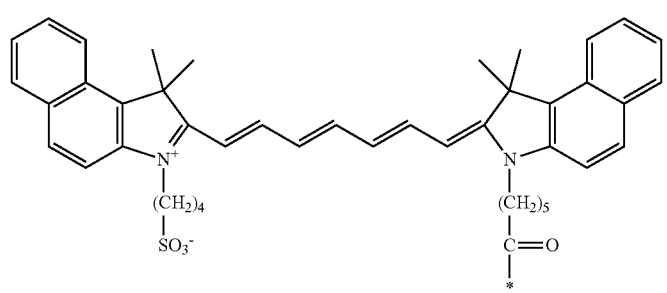

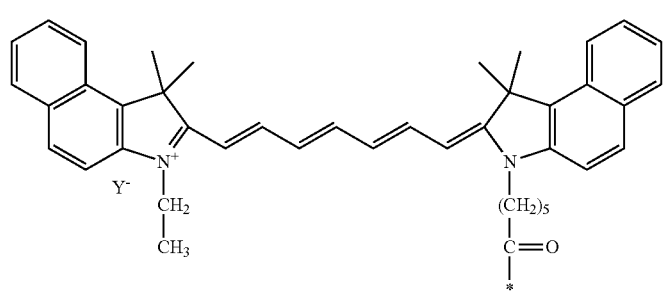

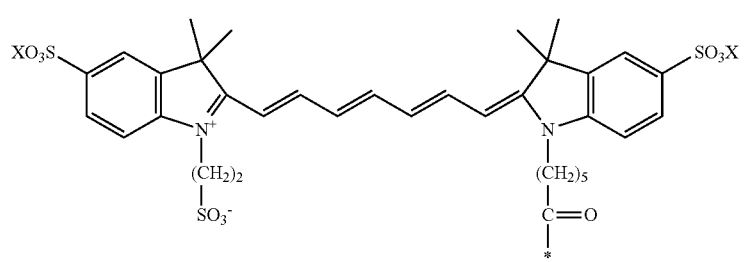

(d1-4)
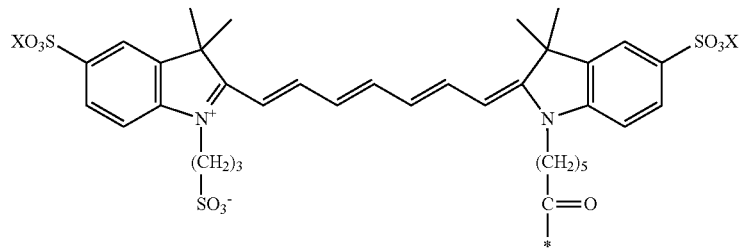

(d1-5)
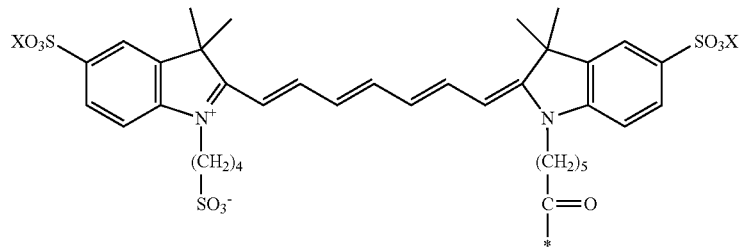

(d1-6)
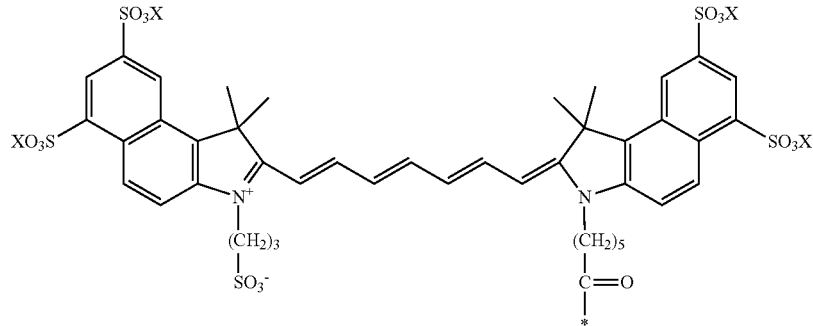

In the formulae (d1-1) to (d1-6), * represents binding to L, or represents direct binding to the carbon atom at the terminal of the repeating unit of formula (P1) or formula (p1-1) when the polymer does not include L.

When L is present, one example of L includes structures including the following formulae (l1) to (l13). In the following formulae (l1) to (l14) two * represent direct binding or indirect binding to the $D_1$ and the $Z_1$, respectively, in the formula (A1); and in the formula (l14), ω represents a residue derived from a terminal after completion of cationic polymerization reaction, or a functional group. The following formulae (l1) to (l14) may be used singly, or the same type of formula or a plurality of formulae may be repeatedly used. An example in which a plurality of formulae are repeatedly used includes the following formula (l1-1). The following formula (l1-1) uses the following formulae (l1), (l2), (l3), (l4), (l5), (l7), (l12) and (l13).

(l1)

(l2)

(l3)

(l4)

(l5)

(l6)

(l7)

(l8)

(l9)

(l10)

(l11)

(112)

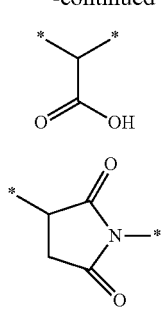

(113)

(114)

(I1-1)

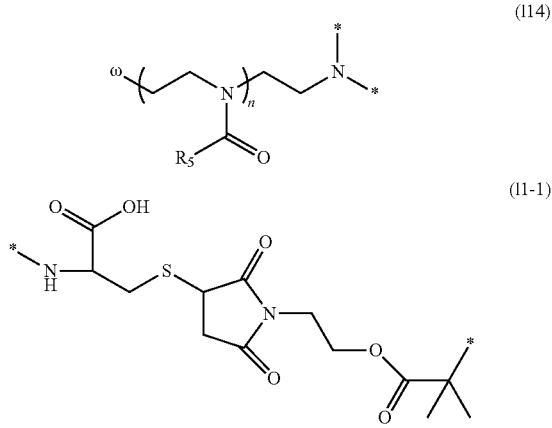

In the above chemical structures, * represents direct binding or indirect binding to D above or the carbon atom at the terminal of the repeating unit.

Formation of L above can be conducted by using, for D above, one having a reactive group such as an amino group, a hydroxyl group, a thiol group, a carboxyl group, an epoxy group, a glycidyl group, an N-succinimidyloxy group, an N-sulfosuccinimidyl group, an N-maleimide alkyl group, an iodoacetamide group, a bromoacetamide group, an isothiocyano group, a sulfonic acid chloride group and a carboxylic acid chloride group, to generate a bond between the reactive groups selected as a combination that allows a binding reaction to occur. When the bond generated above includes a Schiff base and a carbonyl group, such base and carbonyl group can be subjected to reduction to achieve further stabilization of the bond.

Examples of the formula (P1) include a polymer represented by the following formula (1).

The polymer according to the present embodiment can be further represented by the following formula (A1) Polymer represented by the following formula (A1):

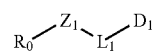

(A1)

In the formula (A1), $R_0$ represents a residue derived from a cationic polymerization initiator, or a functional group; $L_1$ represents a linker and $L_1$ may not be present; $D_1$ represents a dye backbone of a dye having absorption in a near-infrared region; and $Z_1$ represents a structure comprising at least one unit represented by the following formula (A2):

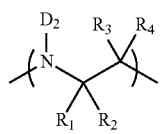

(A2)

In the formula (A2), $D_2$ represents a dye backbone of a dye having absorption in a near-infrared region; and $R_1$ to $R_4$ each independently represent a hydrogen atom, or a substituted or unsubstituted hydrocarbon group having 1 or more and 4 or less carbon atoms, in which, when a substituent is present, the substituent is a functional group including at least one selected from the group consisting of a halogen atom, an oxygen atom and a nitrogen atom.

Furthermore, in the polymer according to the present embodiment, $Z_1$ in the formula (A1) is represented by a structure comprising at least one unit represented by the formula (A2) and at least one unit represented by the following formula (A3):

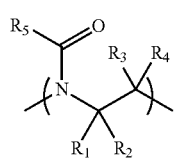

(A3)

In the formula (A3), $R_1$ to $R_4$ each independently represent a hydrogen atom, or a substituted or unsubstituted hydrocarbon group having 1 or more and 4 or less carbon atoms, in which, when a substituent is present, the substituent is a

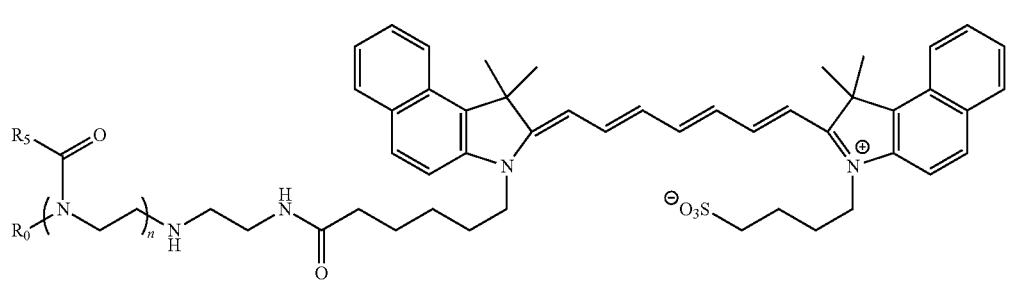

(1)

functional group including at least one selected from the group consisting of a halogen atom, an oxygen atom and a nitrogen atom; and $R_5$ represents any of a methyl group, an ethyl group, an isopropyl group, a n-propyl group, a n-butyl group, a n-octyl group, a n-heptyl group, a phenyl group, a butenyl group and a pentynyl group.

Furthermore, in the polymer according to the present embodiment, $Z_1$ in the formula (A1) can also be represented by a random copolymer having the unit represented by the formula (A2) and the unit represented by the formula (A3).

Examples of a synthesis method for allowing $Z_1$ in the formula (A1) to have the unit represented by the formula (A2) can include a method of allowing the $D_2$ to be bound to an amino group resulting from hydrolysis of polyoxazoline. Examples of the hydrolysis method of polyoxazoline can include a method of adding an aqueous hydrochloric acid or sodium hydroxide solution to an aqueous polyoxazoline solution, followed by warming. The rate of hydrolysis of polyoxazoline can be appropriately adjusted by the concentration of the polymer, the reaction temperature, the reaction time, the amount of the aqueous hydrochloric acid or sodium hydroxide solution or the like. The rate of hydrolysis of polyoxazoline can be measured by the proton NMR method, conductometric titration or the like.

The rate of hydrolysis of the polymer according to the present embodiment can be arbitrarily adjusted for use and is preferably 60% or less, more preferably 20% or less. One cause thereof is as follows: a larger rate of hydrolysis results in a larger proportion of an amino group in the polymer. Amino groups tend to have positive charge and to cause an interaction with cells or other biomaterials. Also, amino groups may cause an interaction of binding with other biomaterials such as proteins. This means that a larger rate of hydrolysis of the polymer results in a larger proportion of an amino group, and hence, the polymer might cause an undesired interaction. It is therefore preferable that the polymer should have the rate of hydrolysis mentioned above.

Examples of a synthesis method for allowing $Z_1$ in the formula (A1) to have the unit represented by the formula (A2) can include a method of allowing the $D_2$ to be bound to an amino group resulting from hydrolysis of polyoxazoline. Hereinafter, the method for allowing the formula (A4) as an example of $D_2$ to be bound will be described.

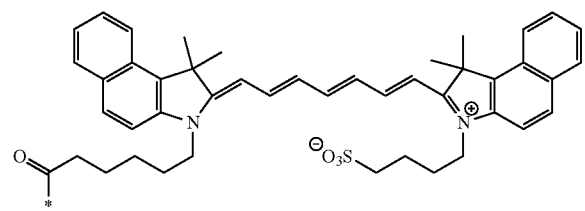

(A4)

In the formula (A4), * represents binding to $L_1$ or N in the formula (A2), or represents binding to $Z_1$ in the formula (A1) when the polymer does not include $L_1$. Specifically, a succinimidyl ester group is first introduced to the formula (A5).

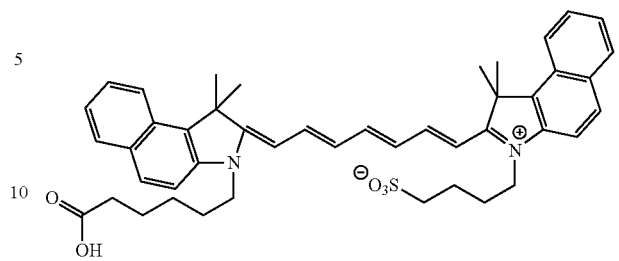

(A5)

Next, the hydrolyzed polyoxazoline can be reacted with the formula (A5) to which a succinimidyl ester group has been introduced to thereby allow the dye to be bound. The introduction method of the dye is not limited to this. As another example, a functional group can be introduced to the hydrolyzed polyoxazoline to allow the dye to be reacted and bound. Furthermore, a reporter molecule, a target-binding molecule or a polymer can be introduced to an amino group resulting from hydrolysis of polyoxazoline. The reporter molecule here means a molecule or a therapeutic agent that generates a physical signal such as a radioactive signal, a magnetic field signal, an ultrasonic signal, a fluorescent signal or an optical ultrasonic signal, and examples include radioactive halogen, radioisotope, a paramagnetic metal ion, an iron oxide particle, a gold nanoparticle, a microbubble, a dye and an anticancer agent. While examples of the dye include a fluorescent compound and a phosphorescent compound, a molecule that generates an optical ultrasonic signal may have the property of absorbing light in the wavelength region depending on the object. The polymer can have the reporter molecule to thereby be utilized as a contrast agent for an enhancement in contrast. The target-binding molecule here means a substance that is selectively bound to a target specific to a tumor and the periphery thereof, and can be arbitrarily selected from compounds such as a biomolecule and a pharmaceutical product. Specific examples include an antibody, an antibody fragment and artificial antibodies such as a single-strand antibody, and an enzyme, bioactive peptide, glycopeptide, a sugar chain, a lipid and a molecule-recognizing compound. Such substances can be used singly or in combinations of a plurality thereof. A compound to which the target-binding molecule is bound can be used to thereby allow a target specific to a tumor and the periphery thereof to be detected, to monitor dynamics, localization, drug efficacy, metabolism and the like. The polymer here means a polymer such as polyethylene glycol. The polymer can be preferably used in control of dynamics in administration to a living body. Although any property of water solubility and hydrophobicity is acceptable, a polymer having water solubility is preferable.

When $Z_1$ in the formula (A1) of the polymer according to the present embodiment is represented by a random copolymer having the unit represented by the formula (A2) and the unit represented by the formula (A3), the ratio of the unit represented by the formula (A2) can be arbitrarily adjusted for use and is preferably 60% or less, more preferably 20% or less, further preferably 0.01% or more and 10% or less. One cause thereof is as follows: a larger ratio of the unit represented by the formula (A2), i.e., a larger ratio of $D_2$, might cause an interaction between $D_2$ and cells or other biomaterials to thereby influence in vivo kinetics.

Furthermore, examples of the polymer of the formula (A1) include a polymer represented by the following formula (A6).

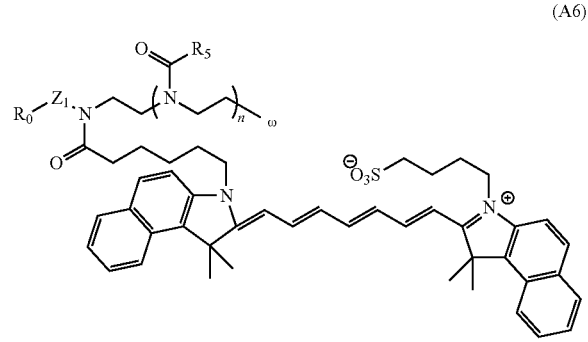

(A6)

In the formula (A6), $R_0$ represents a residue derived from a cationic polymerization initiator, or a functional group; ω represents a residue derived from a terminal after completion of cationic polymerization reaction, or a functional group and is a dye backbone of a dye having absorption in a near-infrared region; and $R_5$ represents any of a methyl group, an ethyl group, an isopropyl group, a n-propyl group, a n-butyl group, a n-octyl group, a n-heptyl group, a phenyl group, a butenyl group and a pentynyl group.

Examples of the unit represented by the formula (A2) include a unit represented by the following formula (A7), and examples of the unit represented by the formula (A3) include a unit represented by the following formula (A8).

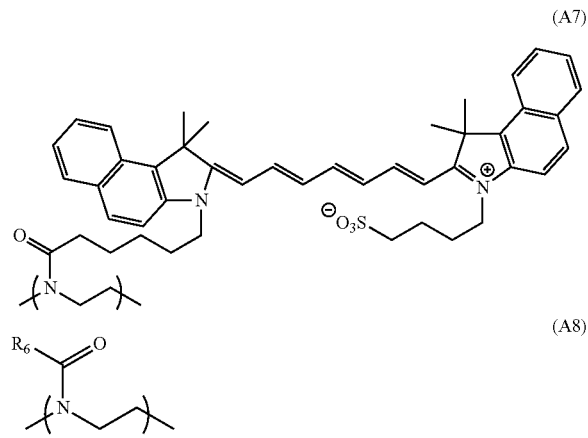

(A7)

(A8)

In the formula (A8), $R_5$ represents any of a methyl group, an ethyl group, an isopropyl group, a n-propyl group, a n-butyl group, a n-octyl group, a n-heptyl group, a phenyl group, a butenyl group and a pentynyl group.

(Polyoxazoline)

OZ according to the present embodiment is also represented as 4,5-dihydro-1,3-oxazole. POZ as the main chain in the present embodiment is a water-soluble polymer, and has the properties of a high biocompatibility and low cytotoxicity. POZ is also expected to be degraded and metabolized in a living body.

The weight average molecular weight of the polymer of the present embodiment is preferably in the range of 10000 or more and 200000 or less, further preferably 10000 or more and 100000 or less, further preferably 10000 or more and 50000 or less, still further preferably 15000 or more and 50000 or less, further more preferably 15000 or more and 30000 or less. When the weight average molecular weight is 10000 or more, the Enhanced Permeability and Retention (hereinafter, sometimes abbreviated as "EPR") effect can allow the polymer to be more accumulated in a tumor site than a normal site in a living body. The molecular weight of the polymer can be 50000 or less because progress of a polymerization reaction is more difficult and the solution viscosity is increased according to an increase in the molecular weight of the polymer. The polymer according to the present embodiment, including POZ having such properties and the dye, and a photoacoustic contrast agent including the polymer are each accumulated in a tumor site and have a rapidly reduced concentration in blood, and therefore exert the effect of increasing the tumor/blood ratio. In the present description, the molecular weight means the weight average molecular weight. The weight average molecular weight can be measured by the GPC method or the proton NMR method.

OZ is a 5-membered ring compound having an iminoether bond in the molecule, and any substituent can be introduced at the 2-position of OZ. Examples can include MeOZ where a methyl group is introduced, EtOZ where an ethyl group is introduced, IPOZ where an isopropyl group is introduced, 2-n-propyl-2-oxazoline where a n-propyl group is introduced, 2-n-butyl-2-oxazoline where a n-butyl group is introduced, 2-n-octyl-2-oxazoline where a n-octyl group is introduced, 2-n-heptyl-2-oxazoline where a n-heptyl group is introduced, 2-phenyl-2-oxazoline where a phenyl group is introduced, 2-(but-3-enyl)-2-oxazoline where a butenyl group is introduced and 2-(pent-4-ynyl)-2-oxazoline where a pentynyl group is introduced. In the present embodiment, MeOZ, EtOZ or IPOZ can be most preferably used as OZ, but OZ is not limited thereto.

OZ is polymerized by a cationic ring-opening polymerization reaction to produce POZ. Any substance that initiates cationic ring-opening polymerization can be used as a polymerization initiator (hereinafter, sometimes abbreviated as an "initiator"), and methyl p-toluenesulfonate or methyl trifluoromethanesulfonate can be used. When such an initiator is used, the terminal of the polymer is a methyl group. OZ above can be polymerized singly or in any combinations. The polymerization can be performed based on a common reaction. Examples include stirring at room temperature, a warming reaction by a reflux apparatus, and a warming reaction by a microwave, and in particular, the reaction by a microwave can be adopted because the reaction can provide POZ having a low dispersibility in a short time. The reaction by a microwave can be controlled at 80 to 200° C. for a reaction time of 1 to 30 minutes to thereby adjust the molecular weight and the dispersibility of the polymer. For the microwave apparatus, any instrument commonly used can be used, and examples can include Discover (registered trademark) SP System (manufactured by CEM Corporation).

POZ exhibits a lower critical solution temperature (hereinafter, sometimes abbreviated as a "LCST") depending on the composition of OZ, the POZ concentration in the solution, and the molecular weight of POZ. LCST is also expressed as a cloud point. For example, PEtOZ is reported to exhibit a LCST of 61 to 72° C., and PIPOZ is reported to exhibit a LCST of 35 to 39° C. POZ is aggregated by reversible phase transition occurring at a temperature equal to or higher than LCST. After being administered into a living body, the polymer according to the present embodiment and the photoacoustic contrast agent including the polymer are circulated in blood and accumulated in a tumor site, but the polymer exhibiting a lower LCST than the LCST of the living body after such administration. POZ cannot be adopted because of being aggregated in the living body. That is, the polymer according to the present embodiment and the photoacoustic contrast agent including the polymer can exhibit a higher LCST than the LCST of the living body after such administration.

The polymer according to the present embodiment is aggregated at a temperature equal to or higher than LCST as mentioned above. Along with this, the photoacoustic signal is increased. This increase can be confirmed to be 3-fold at the maximum, as shown in Examples mentioned later. One possible cause thereof is an effect brought about when the absorbed light/heat energy of the polymer moves to an aggregate polymer layer rather than ambient water. Thus, it is thought to be efficiently converted from absorbed energy of the polymer to the photoacoustic signal. That is, the site at which the polymer according to the present embodiment has been accumulated can be effectively warmed to thereby increase the photoacoustic signal generated from this site.

POZ as the main chain of the polymer according to the present embodiment can be functionalized by introduction of a functional group by any of various methods described below. Examples of a functional group that can be introduced at the α-position, derived from the initiator, include alkyne, alcohol, carboxyl, amine and anthracene. A functional group that can be introduced at the ω-position of POZ, as another example, includes amine, alkene, carboxyl, thiol and azide. Introduction of a functional group at the ω-position can be adopted because of being also conducted by a reaction that progresses with no use of a protective group and of being simple. For example, after the polymerization reaction for providing POZ, a dye having amine as a functional group can be introduced by a nucleophilic reaction to thereby allow the dye to be covalently bound. Furthermore, as one example of introduction of a functional group at the α-position, diamine (for example, ethylenediamine) is reacted to introduce an amino group. Specifically, with respect to the polymer according to the present embodiment and the photoacoustic contrast agent including the polymer, after the polymerization reaction for providing POZ, ethylenediamine is reacted with POZ to introduce an amino group to POZ, and thereafter a dye having a succinimidyl ester group is reacted to allow the dye to be covalently bound, but the introduction method of the dye is not limited thereto. As another example, a functional group that can be introduced at the 2-position of a side chain of POZ includes alkene, alkyne, amine, aldehyde and thiol. Alkyne can be subjected to azide-alkyne cyclic addition by a click reaction. A compound having a thiol group can be added to alkyne by a thiol-ene click reaction. A reporter molecule or a target-binding molecule can be introduced to POZ as the main chain of the polymer by any of the above reactions. The reporter molecule here means a molecule or a therapeutic agent that generates a physical signal such as a radioactive signal, a magnetic field signal, an ultrasonic signal, a fluorescent signal or an optical ultrasonic signal, and examples include radioactive halogen, radioisotope, a paramagnetic metal ion, an iron oxide particle, a gold nanoparticle, a microbubble, a dye and an anticancer agent. While examples of the dye include a fluorescent compound and a phosphorescent compound, a molecule that generates an optical ultrasonic signal may have the property of absorbing light in the wavelength region depending on the object. The polymer can have the reporter molecule to thereby be utilized as a contrast agent for an enhancement in contrast. The target-binding molecule here means a substance that is selectively bound to a target specific to a tumor and the periphery thereof, and can be arbitrarily selected from compounds such as a biomolecule and a pharmaceutical product. Specific examples include an antibody, an antibody fragment and artificial antibodies such as a single-strand antibody, and an enzyme, bioactive peptide, glycopeptide, a sugar chain, a lipid and a molecule-recognizing compound. Such substances can be used singly or in combinations of a plurality thereof. A compound to which the target-binding molecule is bound can be used to thereby allow a target specific to a tumor and the periphery thereof to be detected, to monitor dynamics, localization, drug efficacy, metabolism and the like.

(Near-Infrared Dye)

The dye for use in the present embodiment is a molecule that generates a physical signal such as a fluorescent signal or an optical ultrasonic signal. The polymer according to the present embodiment can have one or more dyes to thereby be used as a diagnostic contrast agent, most preferably as a photoacoustic contrast agent. Examples of the dye include a fluorescent dye, and in particular, a fluorescent dye can be adopted which has the property of absorbing light in the near-infrared wavelength region, the light being relatively high in permeability into a human body. The near-infrared wavelength region here is in the range from 600 nm to 1300 nm. Examples of the near-infrared organic dye in the present embodiment can include an azine type dye, an acridine type dye, a triphenylmethane type dye, a xanthene type dye, a porphyrin type dye, a cyanine type dye, a phthalocyanine type dye, a styryl type dye, a pyrylium type dye, an azo type dye, a quinone type dye, a tetracycline type dye, a flavone type dye, a polyene type dye, a BODIPY (registered trademark) type dye and an indigoid type dye. Other examples can include indocyanine green (ICG), Alexa Fluor (registered trademark) type dyes (produced by Life Technologies Japan) such as Alexa Fluor (registered trademark) 750, a Cy (registered trademark) type dye (produced by GE Healthcare), IR-783, IR-806 and IR-820 (produced by Sigma Aldrich Japan), IR Dye 800CW (registered trademark) and IR Dye 800RS (registered trademark) (produced by LI-COR, Inc.), ADS780WS, ADS795WS, ADS830WS and ADS832WS (produced by American Dye Source Inc.), a DyLight (registered trademark) type dye (produced by Thermo Fisher Scientific K.K.), a Hilyte Fluor (registered trademark) type dye (produced by AnaSpec Inc.), and a DY (registered trademark) type dye (produced by Dyomics GmbH). A dye having a nucleophilic functional group like amine can be adopted because of being capable of being reacted with POZ to form a covalent bond. A functional group like amine can also be introduced to a generally commercially available dye and bound to POZ. The dye can be bound to POZ by any of a non-covalent bond and a covalent bond, or a combination thereof. In the case of administration into a body, it is desirable that the dye and POZ as the main chain be integrated for a certain time or more, and therefore it is desirable that the dye and POZ be bound by a covalent bond in the polymer.

(Contrast Agent for Photoacoustic Imaging)

The contrast agent for photoacoustic imaging according to the present invention includes the polymer singly or includes the polymer and a dispersion medium. Examples of the dispersion medium include saline, distilled water for injection, phosphate buffered saline and an aqueous glucose solution. The photoacoustic contrast agent according to the present invention may also include if necessary a pharmacologically acceptable additive, for example, a vasodilator. The photoacoustic contrast agent according to the present invention may be dispersed in the dispersion medium in advance, or may be in the form of a kit and be dispersed in the dispersion medium for use before administration into a living body. The photoacoustic contrast agent according to the present invention can utilize the EPR effect to thereby be more accumulated in a tumor site than a normal site in a living body in administration thereof into the living body. Furthermore, the concentration in blood is rapidly reduced and therefore the effect of increasing the tumor/blood ratio is exerted. As a result, when the contrast agent is administered into a living body and thereafter the living body is irradiated with light for detection of an acoustic wave, a larger signal can be detected from a tumor site than a normal site. As described above, the photoacoustic contrast agent according to the present invention can be suitably used for imaging a tumor.

(Photoacoustic Imaging Method)

The method for detecting the contrast agent for photoacoustic imaging according to the present invention, administered into a living body, by use of a photoacoustic imaging apparatus is described. Herein, the photoacoustic imaging is a concept including photoacoustic tomography (tomographic method). The method for detecting the contrast agent for photoacoustic imaging according to the present invention includes the following steps (a) and (b). Herein, the photoacoustic imaging method according to the present invention may include other step(s) than the steps shown below:

(a) a step of irradiating a specimen, to which the photoacoustic contrast agent according to the present invention is administered, with light in a wavelength region from 600 nm to 1300 nm, and (b) a step of detecting an acoustic wave emitted from the photoacoustic contrast agent present in the specimen.

The method for detecting the contrast agent for photoacoustic imaging according to the present invention may include a step of reconstructing a spatial photoacoustic signal intensity distribution from the wavelength, phase, time information and the like of the acoustic wave obtained in step (b) above. Herein, three-dimensional image reconstruction can be conducted based on the wavelength, phase and time information of the photoacoustic signal obtained in step (b) above. Data obtained by the image reconstruction may take any form as long as the position information of the intensity distribution of the photoacoustic signal can be grasped from the data. For example, a form may be taken in which the photoacoustic signal intensity is exhibited on a three-dimensional space, or a form may be taken in which the photoacoustic signal intensity is exhibited on a two-dimensional plane. In addition, the following form can also be taken: information on the same observation object is acquired by a different imaging method and the positional correspondence relationship between such pieces of information and the photoacoustic intensity distribution is acquired. In step (a) above, the specimen to which the polymer according to the present embodiment is administered by a method such as oral administration or injection can be used. In step (b) above, an apparatus that emits light with which the specimen is irradiated, and an apparatus that detects the photoacoustic signal emitted from the polymer according to the present embodiment are not particularly limited. A light source for irradiation of the specimen with light in step (b) above is not limited as long as the light source can irradiate the specimen with laser pulse light having at least one wavelength selected from the range from 600 nm to 1300 nm. Examples of the apparatus for irradiating the specimen with laser pulse light include a titanium sapphire laser (LT-2211-PC, manufactured by Lotis TII), an OPO laser (LT-2214 OPO, manufactured by Lotis TII) and an alexandrite laser. The apparatus for detecting the acoustic wave is not particularly restricted and various apparatuses can be used. For example, such detection can be conducted using a commercially available photoacoustic imaging apparatus (Nexus128, manufactured by Endra Inc.).

The imaging method using the contrast agent for photoacoustic imaging according to the present invention can image an objective site such as a tumor or a blood vessel through steps (a) and (b) above.

EXAMPLES

Hereinafter, the present invention is described with reference to Examples in more detail, but the present invention is not limited to such Examples.

Example 1

Example 1 Hilyte Fluor (Registered Trademark) 750-Labeled POZ (Synthesis of Polymer)

(1) Each polyoxazoline (POZ) was synthesized using methyl p-toluenesulfonate as an initiator, using 2-ethyl-2-oxazoline (EtOZ) or 2-isopropyl-2-oxazoline (IPOZ), or EtOZ and IPOZ, as a monomer, and using acetonitrile as a reaction solvent. The ratio of the initiator to the monomer mixed in initiation of the reaction based on a molar number was shown in Table 1. The polymerization reaction for providing POZ was performed by warming under conditions of 140° C. and 14 minutes by use of a microwave apparatus Discover (registered trademark) SP System (manufactured by CEM Corporation). A solution obtained by dissolving Hilyte Fluor (registered trademark) 750 amine (produced by AnaSpec Inc.) as a dye in dimethylsulfoxide (hereinafter, sometimes abbreviated as "DMSO") was admixed with a solution of POZ after the polymerization reaction, and warmed under conditions of 140° C. and 1 minute by use of the microwave apparatus to thereby provide a bound substance of the dye and POZ (hereinafter, sometimes abbreviated as a "polymer"). The solution after the reaction was subjected to distillation off of the solvent under reduced pressure, and the resultant was purified by a column dissolved in N,N-dimethylformamide (hereinafter, sometimes abbreviated as "DMF") and filled with a Sephadex LH-20 (produced by GE Healthcare) resin. Subsequently, Amicon Ultra Centrifugal Filter Units (manufactured by Millipore Corporation) were used for purification by ultrafiltration. Binding of POZ and the dye was confirmed by electrophoresis.

TABLE 1

| Polymer | Type of monomer | Monomer/initiator ratio (mol/mol) | Weight average molecular weight (Da) |
|---|---|---|---|
| P1 | EtOZ | 50 | 2400 |
| P2 | EtOZ | 75 | 3200 |
| P3 | EtOZ | 100 | 5000 |
| P4 | EtOZ:IPOZ = 1:1 | 100 | 4100 |
| P5 | EtOZ | 200 | 11000 |
| P6 | EtOZ | 400 | 21000 |
| P7 | IPOZ | 400 | 17000 |
| P8 | EtOZ:IPOZ = 1:1 | 400 | 20000 |

(Molecular Weight Evaluation)

The molecular weight of each of polymers P1 to P8 prepared was evaluated by a Gel Permeation Chromatography (hereinafter, sometimes abbreviated as "GPC") system (Shimadzu Corporation). Specifically, a GPC system was used which was configured from CBM-20A as a system controller, LC-20AD as a liquid-feeding unit for analysis, DGU-20A3 as an online degasser, CTO-20AC as a column oven, RID-10A as a differential refractive index detector, SPD-20A as a UV-VIS detector, and an LC work station and GPC software. PLgel MIXED-E was used as a column for analysis, and DMF was used as an eluent. Polyethylene glycol ((hereinafter, sometimes abbreviated as "PEG") was used as a standard molecular weight substance for performing calibration. A solution of the bound substance of the dye and POZ in DMF was allowed to flow into the column at a flow rate of 0.5 ml/min, and the molecular weight was calculated from the elution time (Table 1). In Table 1, the monomer/initiator ratio represents the ratio of the molar number of the monomer loaded in the reaction to the molar number of the initiator. The molecular weight was increased according to an increase in the ratio of the monomer loaded.

(Evaluation of Temperature Responsiveness)

Each of polymers P1 to P8 prepared was dissolved in pure water. In order to examine the phase transition temperature of each of polymers P1 to P8, Zetasizer nano-ZS was used to evaluate the particle size at an arbitrary temperature, and a temperature at which the particle size was increased and the solution was clouded was defined as the phase transition temperature. No phase transition could be confirmed even at 75° C. or higher with respect to P1 to P3. Each phase transition temperature was summarized in Table 2. The phase transition temperature was varied depending on the molecular weight of the polymer and the composition of the monomer. A tendency was confirmed in which the phase transition temperature was decreased according to an increase in the molecular weight and an increase in the ratio of IPOZ.

TABLE 2

| Polymer | Phase transition temperature [° C.] | Photoacoustic signal intensity [V/J/M] |
|---|---|---|
| P1 | N.D. | $2.6 \times 10^5$ |
| P2 | N.D. | $2.5 \times 10^5$ |
| P3 | N.D. | $3.2 \times 10^5$ |
| P4 | 52 | $3.1 \times 10^5$ |
| P5 | 72 | $3.8 \times 10^5$ |
| P6 | 70 | $5.2 \times 10^5$ |
| P7 | 35 | $6.4 \times 10^5$ |
| P8 | 45 | $3.6 \times 10^5$ |

(Photoacoustic Evaluation)

Measurement of the acoustic wave, specifically, measurement of the photoacoustic signal intensity was performed as follows: a sample dispersed in PBS was irradiated with pulse laser light, and the intensity of the photoacoustic signal generated from the sample was detected using a piezoelectric element, amplified by a high-speed preamplifier, and acquired by a digital oscilloscope. Specific conditions were as follows. A titanium sapphire laser (LT-2211-PC, manufactured by Lotis TII) was used as a light source. The wavelength was 700 to 1000 nm and variable, and the wavelength around the absorption maximum of the sample was selected in the measurement. The energy density was from about 10 to 20 mJ/cm², the pulse width was about 20 nanoseconds, and the pulse repetition frequency was 10 Hz. As the piezoelectric element for detecting the photoacoustic signal, a non-convergence type ultrasonic transducer (V303, manufactured by Panametrics-NDT) having an element diameter of 1.27 cm and a central band of 1 MHz was used. The measurement vessel was a polystyrene cuvette having an optical path length of 0.1 cm and a sample volume of about 200 µl. The measurement vessel and the piezoelectric element were immersed in a glass vessel filled with water and the distance therebetween was set to be 2.5 cm. As the high-speed preamplifier for amplifying the photoacoustic signal intensity, an ultrasonic preamplifier (Model 5682, manufactured by Olympus Corp.) having an amplification degree of +30 dB was used. The signal amplified was input to a digital oscilloscope (DPO4104, manufactured by Tektronix). The polystyrene cuvette was irradiated with pulse laser light from the outside of the glass vessel. A portion of scattering light generated here was detected by a photodiode, and input as a trigger signal to the digital oscilloscope. The digital oscilloscope was set to a 32 run-averaging display mode to measure the photoacoustic signal intensity on average of 32 laser pulse irradiations. The photoacoustic signal intensity of each of P1 to P8 measured was normalized by the laser intensity and the dye concentration in the polymer solution subjected to the measurement, and summarized in Table 2.

(Evaluation of Tumor Accumulation Property and Evaluation of Concentration in Blood)

The amount of the polymer transferred to a tumor mass was evaluated using a tumor bearing mouse in Examples of the present invention. For the mouse, a female outbred BALB/c slc-nu/nu mouse (6-week-old at the time of purchase) (Japan SLC, Inc.) was used. For one week before inoculation of tumor cells to the mouse, the animals were housed in air-conditioned rooms under a 12-h light/dark cycle and allowed free access to food and water. Mouse rectum cancer cell lines (Colon 26) ($10^6$ cells) were subcutaneously implanted to the mouse, and the mouse was raised until the size of the tumor mass reached 5 to 10 mm. The polymer of the present invention (13 nmol as the amount of the dye) was administered to the tumor bearing mouse, and fluorescence imaging of the tumor bearing mouse at one day after administration was performed. The fluorescence imaging was performed using IVIS (registered trademark) Imaging System. FIG. 1 illustrates the fluorescence image of the tumor bearing mouse at one day after administration of polymer P6 of the present invention. Strong fluorescence was observed from polymer P6 accumulated in the tumor.

In order to confirm the tumor accumulation property of the polymer of the present invention, each of polymer P1, polymer P2, polymer P3, polymer P5, polymer P6 and polymer P8 was administered to the tumor bearing mouse through the tail vein. The amount to be administered was 13 nmol as the amount of the dye. The mouse was euthanized by a carbon dioxide gas one day after administration, and a tumor tissue was resected. An aqueous Triton (registered trademark)-X100 solution was added to the tumor tissue and homogenated, and thereafter DMSO was added thereto to extract the dye, preparing a solution of the dye extracted. On the other hand, a cancer tissue was also resected from a tumor bearing mouse to which nothing was administered, and an aqueous Triton-X100 solution was added thereto to prepare a tumor homogenate solution. Next, a known concentration of each of polymer P1, polymer P2, polymer P3, polymer P5, polymer P6 and polymer P8 was diluted with the tumor homogenate solution to each concentration, and DMSO was added to the dilute solution to prepare a standard liquid for calibration, from which the dye was extracted.

IVIS (registered trademark) Imaging System 200 Series (manufactured by XENOGEN) were used to measure the fluorescence intensity of each of the solution of the dye extracted and the standard liquid for calibration, thereby quantitatively determining the amount of the dye in the tumor tissue. The rate of dye transfer (also referred to as the amount of tumor accumulation, abbreviated as % injected dose: % ID) to the tumor tissue based on the amount to be administered, per unit weight of the tumor tissue, was calculated.

Figure 2:
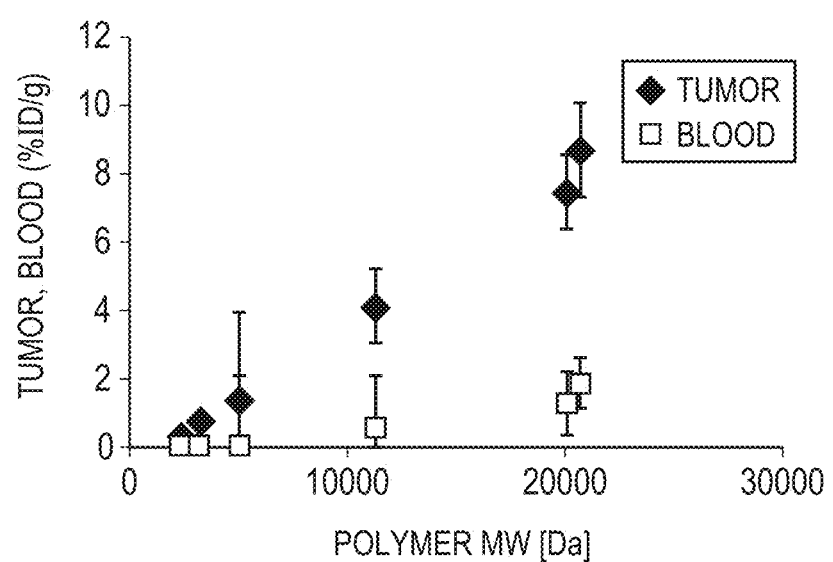
FIG. 2 is a graph illustrating the amount of tumor accumulation and the concentration in blood in administration of each of polymer P1, polymer P2, polymer P3, polymer P5, polymer P6 and polymer P8 in Examples of the present invention, to each mouse.

In the tumor accumulation property evaluation, blood was collected from the tail vein immediately before the mouse was euthanized by a carbon dioxide gas, after one day. The aqueous Triton-X100 solution was added to the blood collected, and DMSO was then added thereto to extract the dye, thereby preparing a blood solution of the dye extracted. On the other hand, a known concentration of each of polymer P1, polymer P2, polymer P3, polymer P5, polymer P6 and polymer P8 was diluted with the aqueous Triton-X100 solution to each concentration, and the solution diluted and the same amount of the blood collected from the mouse to which nothing was administered were mixed. Next, the aqueous Triton-X100 solution and DMSO were further added to the mixed solution with the blood to prepare a standard blood solution for calibration. IVIS (registered trademark) Imaging System 200 Series (manufactured by XENOGEN) were used to measure the fluorescence intensity of each of the blood solution of the dye extracted and the standard blood solution for calibration, thereby quantitatively determining the amount of the dye in blood (% ID/g). The amount of tumor accumulation and the amount of the dye in blood were calculated and plotted against the weight average molecular weight of the polymer administered (FIG. 2). An increase in the amount of tumor accumulation was confirmed according to an increase in the molecular weight of the polymer.

Comparative Example 1 ICG-Labeled Polyethylene Glycol (Synthesis of Bound Substance of Polyethylene Glycol and Dye)

Monoamine linear PEG ME-200EA (produced by NOF Corporation, Mw: 20000) was dissolved in 50 mM carbonate buffer (pH 9.0), and the $NH_2$ concentration was set to be 0.625 mM. On the other hand, 1 mg (1.25 μmol) of ICG-Sulfo-OSu (produced by Dojindo Molecular Technologies, Inc.) was dissolved in 100 μl of DMSO. 20 μl of a solution of ICG-Sulfo-OSu in DMSO was added to carbonate buffer (400 μl) of PEG, and the reaction was performed with the reaction ratio of ICG-Sulfo-OSu to PEG being 1. After rotation and stirring under light shielding at room temperature for 24 hours, the reaction solution was filtered by a 0.22-μm syringe filter to provide a bound substance (hereinafter, abbreviated as PEG1) of PEG and the dye.

Figure 3:
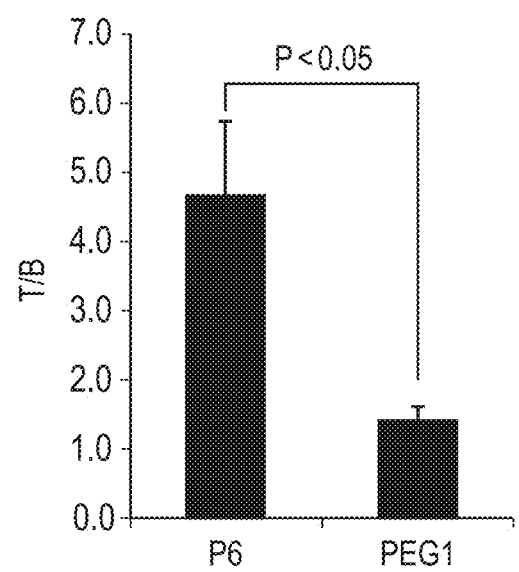
FIG. 3 is a graph illustrating the tumor/blood ratio of each of polymer P6 in Example of the present invention and (PEG1) in Comparative Example.

The amount of tumor accumulation and the amount of the dye in blood of PEG1 were quantitatively determined by the same method as in the polymer of the present invention. With respect to polymer P6 of the present invention, and PEG1, the value obtained by dividing the amount of tumor accumulation by the amount of the dye in blood (hereinafter, abbreviated as the "tumor/blood ratio" or "T/B") was calculated (FIG. 3). Polymer P6 exhibited a significantly high tumor/blood ratio relative to PEG1. The significant test here was performed by the Student's t-test, and P<0.05 was determined as significant.

Example 2

Example 2 ICG-Labeled POZ (Synthesis of Polymer)

Methyl p-toluenesulfonate used as an initiator and EtOZ used as a monomer were mixed in a monomer:initiator ratio=400:1, and a polymer was synthesized using acetonitrile as a reaction solvent. The polymerization reaction was performed by warming under conditions of 140° C. and 14 minutes by use of the microwave apparatus. Subsequently, ethylenediamine was admixed with a POZ solution after the polymerization reaction, and warmed under conditions of 140° C. and 7 minutes by use of the microwave apparatus. The solution after the reaction was subjected to distillation off of the solvent under reduced pressure, and the resultant was dissolved in methanol and dialyzed to methanol using Pre-treated RC Tubing (MWCO: 3.5 kD, manufactured by Spectrum Laboratories, Inc.) for purification, to provide POZ to which an amino group was introduced. Next, the solution after dialysis was subjected to distillation off of the solvent under reduced pressure, the resultant was dissolved in 50 mM borate buffer (pH 8.5) and admixed with ICG-sulfo-OSu (produced by Dojindo Laboratories) dissolved in DMSO, and the reaction was performed under light shielding at room temperature for 24 hours. The solution after the reaction was dialyzed to methanol using Pre-treated RC Tubing described above, for purification, to provide ICG-labeled POZ (hereinafter, referred to as "P9"). Binding of POZ and ICG was confirmed by electrophoresis.

(Molecular Weight Evaluation)

The molecular weight of polymer P9 of the present invention was evaluated by the above GPC system. PLgel MIXED-E was used as a column for analysis, and DMF was used as an eluent. Polyethylene glycol (hereinafter, sometimes abbreviated as "PEG") was used as a standard molecular weight substance for performing calibration. A solution of the bound substance of the dye and POZ in DMF was allowed to flow into the column at a flow rate of 0.5 ml/min, and the molecular weight was calculated from the elution time. As a result, the weight average molecular weight of P9 was 14000.

(Evaluation of Tumor Accumulation Property and Evaluation of Concentration in Blood)

Figure 4:
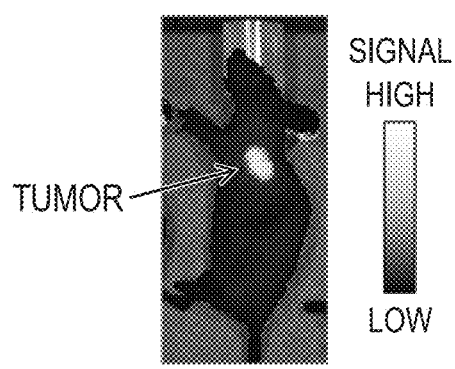
FIG. 4 illustrates a whole-body fluorescence image of a tumor bearing mouse at 24 hours after administration of polymer P9 in Example of the present invention.

Polymer P9 (7.5 nmol) of the present invention was administered to the tumor bearing mouse provided by the above method, and fluorescence imaging of the tumor bearing mouse at one day after administration was performed in the same manner as in the above method. FIG. 4 illustrates the result obtained by administering polymer P9 of the present invention to the tumor bearing mouse, and taking the whole-body fluorescence image after one day. Strong fluorescence was observed from polymer P9 accumulated in a tumor. Furthermore, the amount of tumor accumulation and the amount of the dye in blood of polymer P9 of the present invention were quantitatively determined by the above method. As a result, the amount of tumor accumulation was 10.8±2.1% ID/g, the amount of the dye in blood was 5.5±1.0% ID/g, and thus a high tumor accumulation property was confirmed. In addition, the tumor/blood ratio was 2.0±0.1, and polymer P9 exhibited a significantly high tumor/blood ratio relative to PEG1. The significant test here was performed by the Student's t-test, and P<0.05 was determined as significant.

Reference Example: In Vivo Kinetic Evaluation of POZ (Synthesis of Polymer)

Methyl p-toluenesulfonate used as an initiator, and EtOZ, IPOZ or 2-n-propyl-2-oxazoline (hereinafter, sometimes abbreviated as "NPOZ"), or a combination thereof used as a monomer were mixed in each monomer/initiator ratio shown in Table 3, and a polymer was synthesized using acetonitrile as a reaction solvent. The polymerization reaction was performed by warming under conditions of 140° C. and 14 minutes by use of the microwave apparatus. Subsequently, ethylenediamine was admixed with a POZ solution after the polymerization reaction, and warmed under conditions of 140° C. and 7 minutes by use of the microwave apparatus. The solution after the warming was subjected to distillation off of the solvent under reduced pressure, and the resultant was dissolved in methanol and dialyzed to methanol using Pre-treated RC Tubing (MWCO: 3.5 kD, manufactured by Spectrum Laboratories, Inc.) for purification, to provide POZ to which an amino group was introduced. The molecular weight of the resulting polymer was evaluated by the above GPC system, and the result was summarized in Table 3.

The polymer prepared was dissolved in Phosphate Buffered saline (PBS), and the phase transition temperature was examined as described above. Each phase transition temperature was summarized in Table 3. When the monomer was EtOZ, no phase transition could be confirmed even at 70° C. or higher. On the other hand, when the monomer was NPOZ, a tendency was confirmed in which the phase transition temperature was decreased as compared with the case of IPOZ. When the monomer was a combination of NPOZ and IPOZ, a tendency was confirmed in which the phase transition temperature was decreased according to an increase in the ratio of NPOZ.

Next, radioactive labeling was performed for in vivo kinetic evaluation of the polymer prepared. Specifically, each of polymers P13, P18 and P19, and S-2-(4-Isothiocyanatobenzyl)-1,4,7,10-tetraazacyclododecane tetraacetic acid (also referred to as "p-SCN-Bn-DOTA", produced by Macrocyclics Inc.) were first mixed in methanol in a ratio of polymer:p-SCN-Bn-DOTA=1:5, and the reaction was performed at room temperature for 1.5 days to introduce a metal chelate moiety to the polymer. Hereinafter, polymers P13, P18 and P19, to which the metal chelate moiety was introduced, are referred to as "DOTA-P13", "DOTA-P18" and "DOTA-P19" respectively. In order to remove the unreacted p-SCN-Bn-DOTA, purification was conducted by gel filtration using a PD-10 column (manufactured by GE Healthcare Japan) and ultrafiltration using Amicon Ultra Centrifugal Filter Units.

It was confirmed that the phase transition temperature of each of the polymers, to which the metal chelate moiety was introduced, was not largely changed before and after the introduction.

DOTA-P13 or DOTA-P18 was admixed with $^{111}$InCl$_3$ in acetate buffer, and reacted at room temperature for 10 minutes to provide $^{111}$In-labeled DOTA-P13 (hereinafter, sometimes referred to as "$^{111}$In-labeled DOTA-P13") or $^{111}$In-labeled DOTA-P18 (hereinafter, sometimes referred to as "$^{111}$In-labeled DOTA-P18"). DOTA-P19 was admixed with $^{111}$InCl$_3$ in acetate buffer, and reacted on ice for 10 minutes to provide $^{111}$In-labeled DOTA-P19 (hereinafter, sometimes referred to as "$^{111}$In-labeled DOTA-P19"). The radiochemical yield and the radiochemical purity of each of the resulting polymers were summarized in Table 4. The radioactivity was measured by a NaI well type scintillation counter 1470WIZARD (manufactured by PerkinElmer Co., Ltd.).

TABLE 4

| Polymer | Radiochemical yield (%) | Radiochemical purity (%) |
|---|---|---|
| $^{111}$In-labeledDOTA-P13 | 58.2 | 99.6 |
| $^{111}$In-labeledDOTA-P18 | 51.2 | 99.5 |
| $^{111}$In-labeledDOTA-P19 | 28.6 | 99.7 |

Figure 5A:
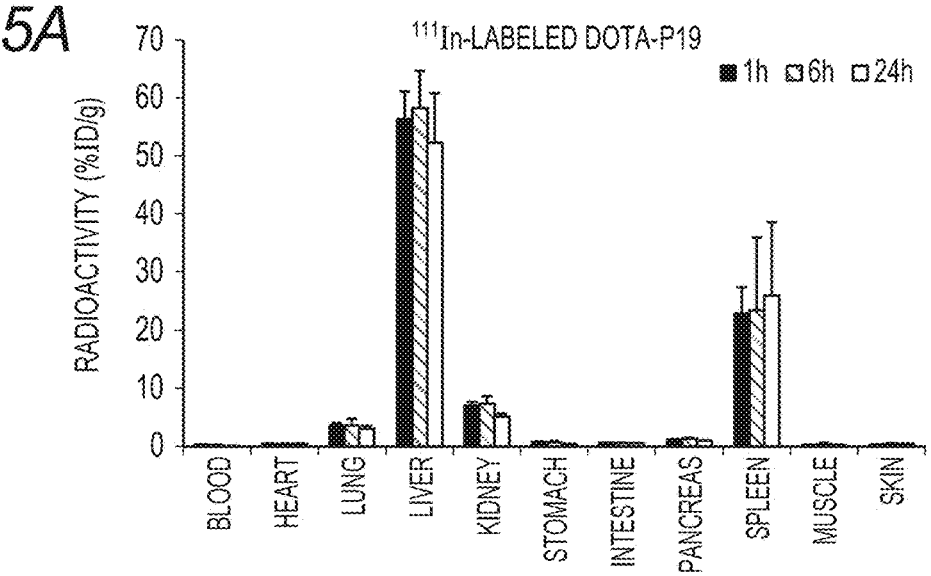
FIGS. 5A, 5B and 5C illustrate graphs illustrating the radioactivity of each organ resected from a mouse at each of 1, 6 and 24 hours after intravenous administration of each of $^{111}$In-labeled DOTA-P13, $^{111}$In-labeled DOTA-P18 and $^{111}$In-labeled DOTA-P19 in Examples of the present invention.

$^{111}$In-labeled DOTA-P13, $^{111}$In-labeled DOTA-P18 or $^{111}$In-labeled DOTA-P19 prepared as above was administered through the tail vein of each mouse (0.6 µCi, 26.7 M (polymer concentration), 150 µL PBS, per mouse), the mouse was euthanized after 1, 6 or 24 hours, the tissue of the mouse was resected, and the weight and the radioactivity thereof were measured. The radioactivity of each organ measured was normalized by the weight of each organ and the radioactivity of a sample administered, and summarized in FIGS. 5A to 5C. $^{111}$In-labeled DOTA-P19 having a lower phase transition temperature than the body temperature of the mouse as a subject was accumulated in the liver and the spleen since one hour after administration, and rapidly cleared from blood (FIG. 5A). It is known that a relatively large molecule is phagocytized by macrophage and aggre-

TABLE 3

Figure 5B:
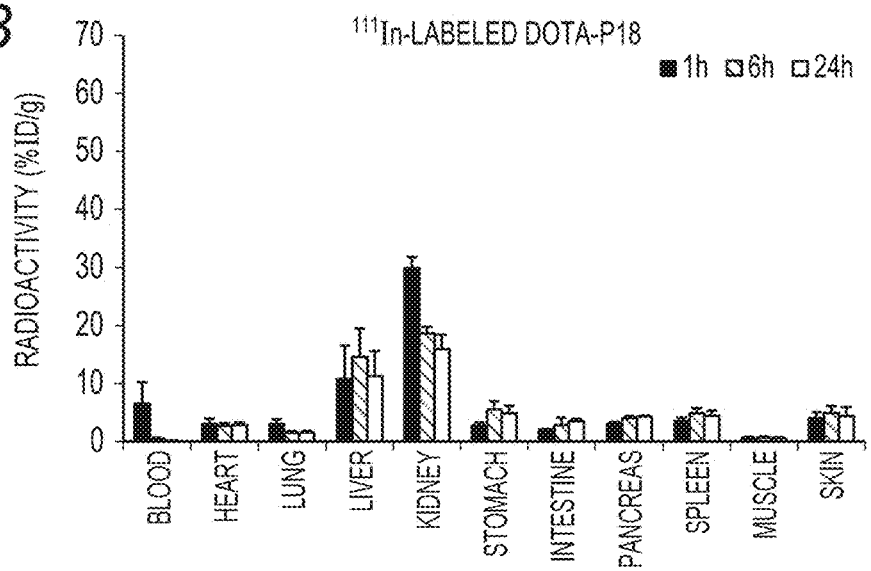
Figure 5C:
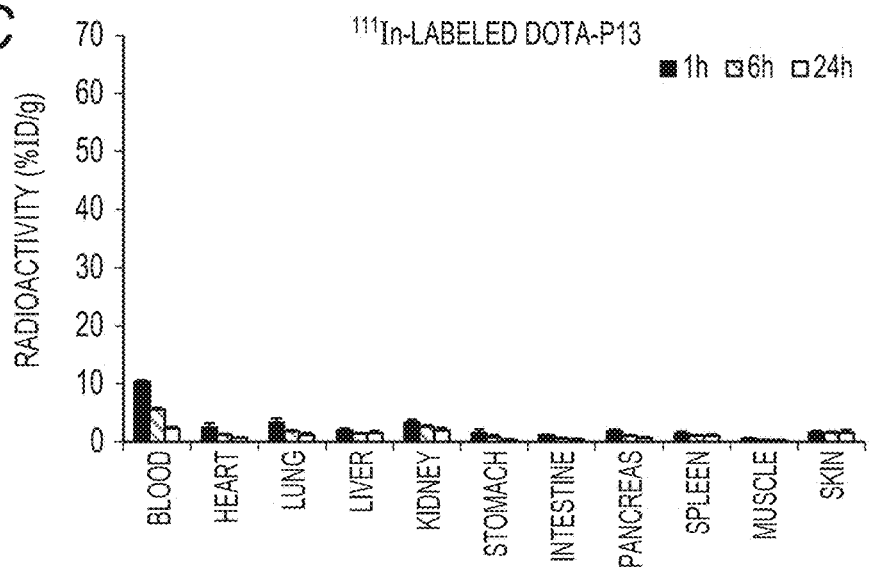

| Polymer | Type of monomer | Concentration (mol/L) | Monomer/initiator ratio (mol/mol) | Weight average molecular weight (Da) | Phase transition temperature (° C.) |
|---|---|---|---|---|---|
| P10 | EtOZ | 3 | 400/1 | 7700 | N.D. |
| P11 | EtOZ | 4 | 400/1 | 12400 | N.D. |
| P12 | EtOZ | 5 | 400/1 | 15800 | N.D. |
| P13 | EtOZ | 7 | 400/1 | 19900 | N.D. |
| P14 | EtOZ | 8 | 400/1 | 31000 | N.D. |
| P15 | IPOZ | 3 | 400/1 | 5300 | 37 |
| P16 | IPOZ | 4.5 | 400/1 | 11900 | 37 |
| P17 | IPOZ | 5 | 400/1 | 17200 | 34 |
| P18 | IPOZ | 6 | 500/1 | 17900 | 35 |
| P19 | NPOZ | 6 | 500/1 | 17700 | 19 |
| P20 | NPOZ/IPOZ | 6 | NPOZ/IPOZ/Initiator = 300/200/1 | 17700 | 25 |
| P21 | NPOZ/IPOZ | 6 | NPOZ/IPOZ/Initiator = 200/300/1 | 17000 | 28 |
| P22 | NPOZ/IPOZ | 6 | NPOZ/IPOZ/Initiator = 100/400/1 | 18000 | 31 | gated in the liver and the spleen, and it is considered with respect to $^{111}$In-labeled DOTA-P19 that the polymer was aggregated in the body of the mouse and therefore accumulated in such organs. Next, $^{111}$In-labeled DOTA-P18 having almost the same phase transition temperature as the body temperature of the mouse as a subject was accumulated in the liver and the kidney, and was present in blood even after one hour of administration (FIG. 5B). Finally, $^{111}$In-labeled DOTA-P13 having a sufficiently higher phase transition temperature than the body temperature of the mouse as a subject did not exhibit a remarkable accumulation in each organ, and was present in blood for a longer time than $^{111}$In-labeled DOTA-P18 and $^{111}$In-labeled DOTA-P19 (FIG. 5C).

Next, $^{111}$In-labeled DOTA-P13, $^{111}$In-labeled DOTA-P18 or $^{111}$In-labeled DOTA-P19 was intratumorally administered (0.6 μCi, 2000 μM (polymer concentration), 5 μL PBS, per mouse) to each mouse bearing human hepatic cancer cells PC-3, the mouse was euthanized after one day, the tumor was resected, and the radioactivity thereof was measured and normalized by the radioactivity of a sample administered. As a result, retention in the tumor was more observed in the order of $^{111}$In-labeled DOTA-P19 (58.8% ID±14.1), $^{111}$In-labeled DOTA-P18 (13.1% ID±3.5) and $^{111}$In-labeled DOTA-P13 (3.3% ID±0.6). It is considered that such an order is achieved because aggregation occurs to make diffusion hard when the phase transition temperature is lower than the body temperature of the subject.

In order to distinctly image a tumor, it is preferable that the amount of tumor accumulation of the polymer (contrast agent) be increased and the concentration of the polymer in blood be decreased. When the polymer is accumulated in a tumor by the EPR effect, the polymer is required to be leaked from a blood vessel to a tumor stroma. Therefore, preferably, the polymer is retained in blood for a certain time after administration. It has been indicated from the experiment of Reference Example above that when a polymer having a higher phase transition temperature than the body temperature of the subject is used, the polymer is present in blood for a certain time after administration. That is, it is indicated that, in order to more distinctly image a tumor, more preferably, a polymer (EtOZ in the present Example) having a higher phase transition temperature than the body temperature of the subject is used.

Example 3: In Vivo Kinetic Evaluation of POZ Having Different Molecular Weight (Synthesis of Polymer)

The polymer was synthesized by the same method as in Example 2 above. The reaction conditions and molecular weight of the polymer are summarized in Table 5.

TABLE 5

| Polymer | Type of monomer | Concentration (mol/L) | Monomer/ initiator ratio (mol/mol) | Weight average molecular weight (Da) | Phase transition temperature (° C.) |
| --- | --- | --- | --- | --- | --- |
| P23 | EtOZ | 7.5 | 400/1 | 26000 | N.D. |

Each of the obtained polymer (P23) and P10, P11, P12 and P14 (0.5 μmol each) synthesized in Example 2 above was admixed with a dye (1 μmol) represented by the formula (d1-1-1) below, 1-ethyl-3-(3-dimethylaminopropyl) carbodiimide hydrochloride (1 μmol) and N,N-dimethyl-4-aminopyridine (1 μmol) in chloroform (1 mL), and the reaction was performed under light shielding for 24 hours. The unreacted dye was removed for purification by dialysis to methanol using Pre-treated RC Tubing (MWCO: 3.5 kD). Hereinafter, the dye-bound P10, P11, P12, P14 and P23 obtained by the above method are referred to as P10-ICG, P11-ICG, P12-ICG, P14-ICG and P23-ICG, respectively. The binding between POZ and the dye was confirmed by electrophoresis. P10-ICG, P11-ICG, P12-ICG, P14-ICG and P23-ICG were all obtained with a purity as high as 99% or more.

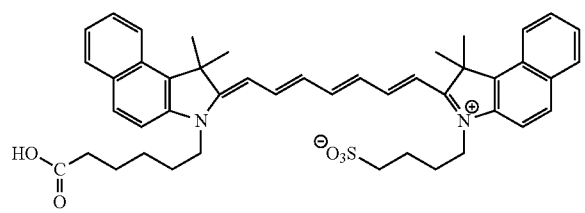

(Evaluation of Tumor Accumulation Property and Evaluation of Concentration in Blood)

Figure 6:
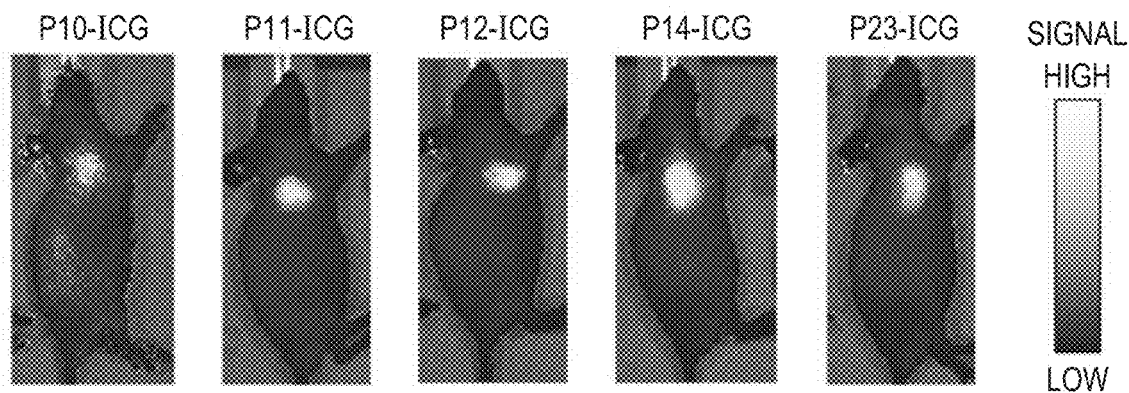
FIG. 6 illustrates a whole-body fluorescence image of a cancer-bearing mouse at 24 hours after administration of polymers P10-ICG, P11-ICG, P12-ICG, P14-ICG and P23-ICG in Examples of the present invention.

P10-ICG, P11-ICG, P12-ICG, P14-ICG or P23-ICG (13 nmol) was administered to the tumor bearing mouse provided by the above method, and fluorescence imaging of the tumor bearing mouse one day after administration was performed in the same manner as in the above method. FIG. 6 illustrates the result obtained by administering P10-ICG, P11-ICG, P12-ICG, P14-ICG or P23-ICG in Examples of the present invention to the tumor bearing mouse, and taking the whole-body fluorescence image after one day. All of the polymers were accumulated in a tumor, and strong fluorescence was observed. Furthermore, the amount of tumor accumulation and the amount of the dye in blood of P10-ICG, P11-ICG, P12-ICG, P14-ICG or P23-ICG in Examples of the present invention were quantitatively determined by the above method. The results are summarized in Table 6. The amount of tumor accumulation generally tended to be increased with an increase in the molecular weight. In addition, the tumor/blood ratio was 3 or more for all of the polymers, and these polymers exhibited a significantly high tumor/blood ratio relative to PEG1 synthesized in Comparative Example 1. The significant test here was performed by the Student's t-test, and P<0.05 was determined as significant.

TABLE 6

| Polymer | Amount of tumor accumulation (% ID/g) | Concentration in blood (% ID/g) | Tumor/blood ratio |
| --- | --- | --- | --- |
| P10-ICG | 3.4 ± 1.2 | 0.6 ± 0.1 | 5.9 ± 2.2 |
| P11-ICG | 10.0 ± 0.3 | 1.0 ± 0.5 | 11.8 ± 6.9 |
| P12-ICG | 11.2 ± 2.1 | 2.6 ± 0.4 | 4.4 ± 1.4 |
| P14-ICG | 12.5 ± 2.4 | 4.9 ± 0.8 | 3.2 ± 0.4 |
| P23-ICG | 11.5 ± 0.7 | 3.7 ± 0.4 | 3.1 ± 0.3 |

Figure 7A:
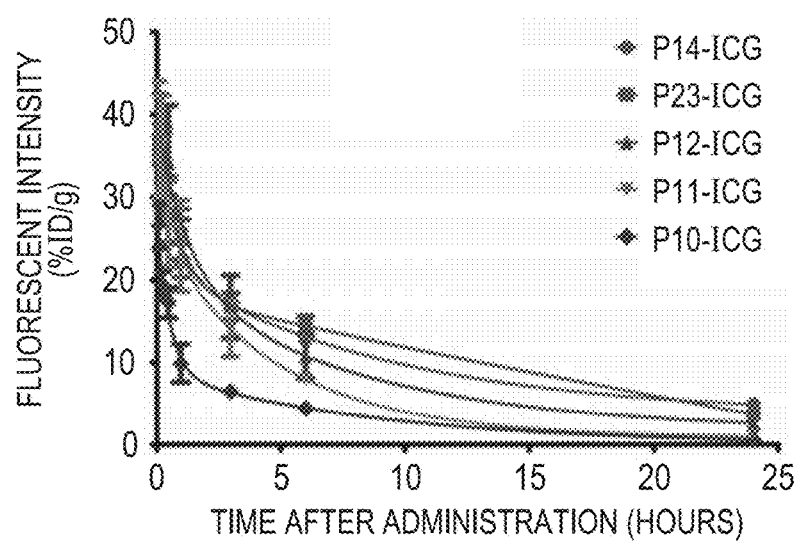
FIGS. 7A and 7B are graphs illustrating a change in the concentration in blood in a cancer-bearing mouse after administration of polymers P10-ICG, P11-ICG, P12-ICG, P14-ICG and P23-ICG in Examples of the present invention.
Figure 7B:
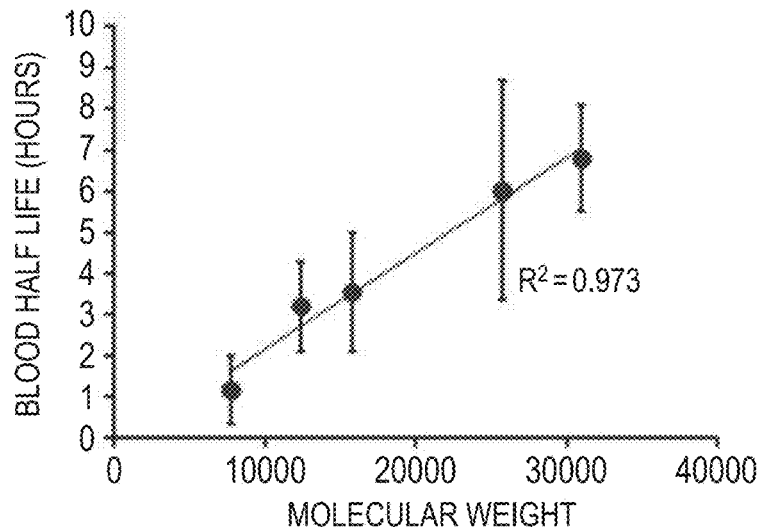

Next, P10-ICG, P11-ICG, P12-ICG, P14-ICG or P23-ICG in Examples of the present invention was administered to the tumor bearing mouse, and blood was collected from the tail vein of the mouse at 5 minutes, 15 minutes, 30 minutes, 1 hour, 3 hours, 6 hours and 24 hours after administration. The dye-bound polymer of the present invention contained in blood was quantitatively determined according to the above method to examine a time-dependent change (FIG. 7A). The half-time in blood was calculated in two phase decay models using GraphPad prism software (produced by GraphPad Software, Inc.) and plotted against the molecular weight of each polymer (FIG. 7B). The results of FIG. 7A showed that the concentration in blood was gradually decreased with an increase in the molecular weight. This is also supported by an increase in the half-time in blood in response to the molecular weight, as illustrated in FIG. 7B.

Example 4: Increase in Photoacoustic Signal Due to Polymer Aggregation (In Vitro Photoacoustic Signal Measurement)

P4 to P8 prepared in Example 1 were evaluated for a change in the photoacoustic signal by the same method as in the above measurement of photoacoustic signal intensity except that the temperature of water in a water bath for measurement was changed to 37° C., 47° C. and 57° C. The results are summarized in Table 7. For P5 and P6 having a phase transition temperature of 70° C. or higher, the photoacoustic signal was increased only about 1.3-fold at the maximum even by warming up to 57° C. This is probably due to an increase in the coefficient of thermal expansion caused by a rise in the water temperature and an increase in the photoacoustic signal caused by the resultant increase in the Gruneisen parameter. On the other hand, the photoacoustic signal was increased 1.5-fold or more at 57° C. for P4, at 37° C. or higher for P7 and at 47° C. or higher for P8. This revealed that the effect of increasing the photoacoustic signal is obtained by aggregation at a temperature equal to or higher than the phase transition temperature. One possible cause thereof is an effect brought about when the absorbed light energy moves to an aggregate polymer layer rather than ambient water. Thus, it can be considered that the conversion efficiency from the absorbed energy of the polymer to the photoacoustic signal becomes higher.

TABLE 7

| Polymer | Phase transition temperature (° C.) | Change in photoacoustic signal intensity (Post/Pre (25° C.) ratio) | | |
|---|---|---|---|---|
| | | 37° C. | 47° C. | 57° C. |
| P4 | 52 | 1.17 ± 0.08 | 1.47 ± 0.10 | 1.58 ± 0.16 |
| P5 | 72 | 1.05 ± 0.21 | 1.02 ± 0.04 | 1.26 ± 0.09 |
| P6 | 70 | 1.23 ± 0.10 | 1.23 ± 0.08 | 1.34 ± 0.05 |
| P7 | 35 | 1.64 ± 0.17 | 3.29 ± 0.53 | 2.48 ± 0.12 |
| P8 | 45 | 1.14 ± 0.12 | 2.28 ± 0.19 | 2.74 ± 0.16 |

Example 5: Oxazoline Side Chain Hydrolysate (Hydrolysis Reaction)

In an embodiment of the present invention, a functional group may be introduced at the 2-position of oxazoline by hydrolysis of a side chain at this position. Specifically, conversion to secondary amine can be performed by hydrolysis or the like. The hydrolysis reaction was performed by the following method using hydrochloric acid (hereinafter, sometimes abbreviated as HCl) or sodium hydroxide (hereinafter, sometimes abbreviated as NaOH): an ethyl-oxazoline polymer (weight average molecular weight: 25000, 50000 or 200000) and HCl or NaOH were mixed at the ratio described in Table 8 in water and warmed at varying temperatures. The solution reacted with NaOH was neutralized with HCl after reaction and dialyzed for purification using Pre-treated RC Tubing (MWCO: 3.5 kD) Three dialysis runs were performed with water for the first run, water:methanol=1:1 for the second run and methanol for the third run used as external solutions. On the other hand, the solution reacted with HCl was neutralized with NaOH after reaction, freeze-dried overnight, and then dissolved in chloroform, and the resultant was recovered by filtration through Celite (registered trademark). The rate of hydrolysis was measured by NMR and electric conductivity. For the electric conductivity, a titration curve was prepared by adding 5 µL of 1 M sodium hydroxide to 0.01 M hydrochloric acid, and based on this curve, the amount of an amino group (which corresponds to the rate of hydrolysis) in the measurement solution was calculated. A tendency was found in which the rate of hydrolysis was in general agreement between the case of calculation by NMR and the case of calculation by electric conductivity. In the case of hydrolysis using NaOH, a tendency was found in which the rate of hydrolysis was increased with increases in the amount of NaOH and the reaction time. On the other hand, the preparation such that the proportion of NaOH added was 10 times the amount of the polymer side chain resulted in a lower rate of hydrolysis than that of the preparation such that the proportion of NaOH added was once the amount of the polymer side chain. This is probably because the polymer concentration was not high. In the case of hydrolysis using HCl, as with the case of NaOH, the rate of hydrolysis was also increased with increases in the reaction time and the proportion of HCl added. Thus, POZ having an expected rate of hydrolysis can be prepared by warming under various conditions using various concentrations of the polymer and NaOH or HCl.

TABLE 8

| Polymer | Average molecular weight | Polymer concentration (mg/mL) | Acid or base | HCl or NaOH:polymer side chain (mol:mol) | Reaction time (hours) | Reaction temperature (° C.) | Rate of hydrolysis (%) | |
|---|---|---|---|---|---|---|---|---|
| | | | | | | | NMR | Electrical conductivity |
| P24 | 25000 | 125 | NaOH | 0.05:1 | 24 | 100 | 0.7 | 0.9 |
| P25 | 25000 | 125 | NaOH | 0.1:1 | 24 | 100 | 1.3 | 1.2 |
| P26 | 25000 | 125 | NaOH | 0.2:1 | 24 | 100 | 1.7 | 2.4 |
| P27 | 25000 | 125 | NaOH | 0.2:1 | 72 | 125 | 2.1 | 3.3 |
| P28 | 25000 | 10 | NaOH | 0.2:1 | 72 | 125 | 2 | 3 |
| P29 | 25000 | 10 | NaOH | 1:1 | 72 | 125 | 6 | 6.3 |
| P30 | 25000 | 7.8 | NaOH | 10:1 | 72 | 125 | 4.9 | 3.2 |
| P31 | 25000 | 50 | HCl | 0.4:1 | 72 | 125 | 37.5 | 42.8 |
| P32 | 25000 | 25 | HCl | 0.4:1 | 72 | 125 | 33.6 | 32.9 |
| P33 | 25000 | 25 | HCl | 0.08:1 | 24 | 125 | 3 | 2.7 |
| P34 | 25000 | 25 | HCl | 0.4:1 | 24 | 125 | 20.9 | 20.1 |
| P35 | 25000 | 25 | HCl | 0.8:1 | 24 | 125 | 51 | 29.3 |

TABLE 8-continued

| Polymer | Average molecular weight | Polymer concentration (mg/mL) | Acid or base | HCl or NaOH:polymer side chain (mol:mol) | Reaction time (hours) | Reaction temperature (° C.) | Rate of hydrolysis (%) NMR | Electrical conductivity |
|---|---|---|---|---|---|---|---|---|
| P36 | 50000 | 25 | HCl | 0.4:1 | 24 | 125 | 40.6 | 20.1 |
| P37 | 50000 | 25 | HCl | 0.16:1 | 24 | 125 | 5.2 | 5.5 |
| P38 | 50000 | 25 | HCl | 0.4:1 | 24 | 100 | 23.5 | 15.6 |
| P39 | 50000 | 25 | HCl | 0.28:1 | 24 | 100 | 11.7 | 11.9 |
| P40 | 50000 | 25 | HCl | 0.16:1 | 24 | 100 | 8.7 | 5.9 |
| P41 | 200000 | 25 | HCl | 0.4:1 | 24 | 125 | 25.5 | 25.6 |
| P42 | 200000 | 25 | HCl | 0.16:1 | 24 | 125 | 4.5 | 3.7 |

(Dye Labeling Reaction of Side Chain)

The hydrolyzed side chains of some polymers of Table 8 above were each labeled with a dye. Specifically, each polymer was admixed with ICG-sulfo-OSu at the ratio described in Table 9 in chloroform, and the reaction was performed under light shielding for 24 hours. In another dye labeling method, each polymer was admixed with a dye represented by the formula (d1-1-1), 1-ethyl-3-(3-dimethylaminopropyl) carbodiimide hydrochloride and N,N-dimethyl-4-aminopyridine in chloroform, and the reaction was performed under light shielding for 24 hours. For both of the dye labeling reactions, the unreacted dye was removed for purification by dialysis to methanol using Pre-treated RC Tubing (MWCO: 3.5 kD). Hereinafter, the dye-bound polymers obtained by the above method are designated as the number of each polymer combined with ICG as described in Table 9. The same polymers differing in the number of bound ICG are distinguished therebetween by the numeral attached to the end. The number of bound ICG was calculated from the polymer weight and absorbance. The binding between the polymer and ICG was confirmed by electrophoresis. The polymers were all obtained with a purity of 90% or more.

(Evaluation of Cellular Uptake)

Figure 8:
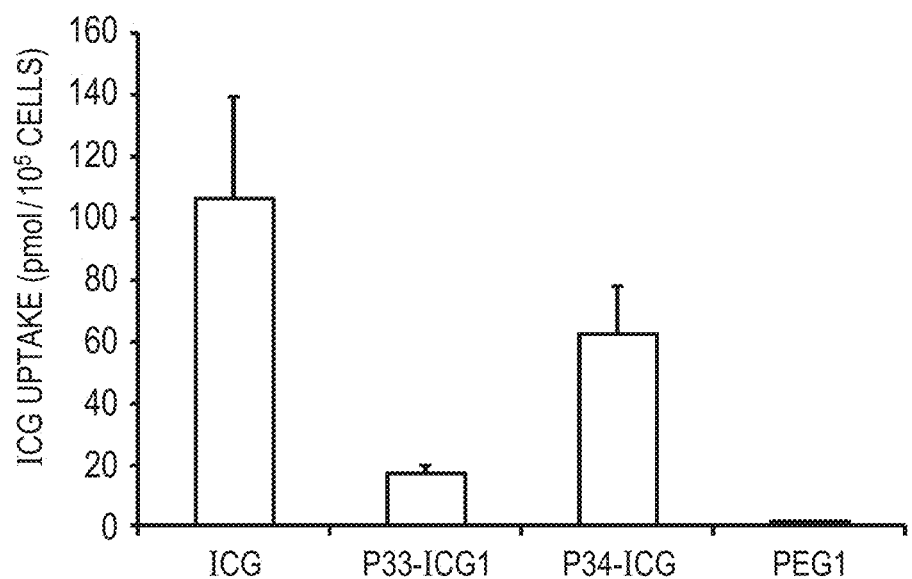
FIG. 8 illustrates cellular uptake experiment results of polymers P33-ICG1 and P34-ICG in Examples of the present invention.

The above polymers P33-ICG1 and P34-ICG were subjected to evaluation of cellular uptake. Colon 26 cells ($10^5$ cells/well) were inoculated to a 24-well cell culture plate and cultured for 1 day in a $CO_2$ incubator. After replacement with a fresh medium (400 μL), P33-ICG1, P34-ICG, ICG, or PEG1 of Comparative Example 1 above (each dye concentration: 10 μM or 100 μL) was added to each well, and the cells were cultured for 24 hours in a $CO_2$ incubator. The solution in each well after culture was discarded, and the well was washed with PBS (1 mL) twice. The cells were recovered by dissociation with a trypsin/ethylenediaminetetraacetic acid solution, and the number of cells per well was measured. Triton X-100 (final concentration: 1%) and DMSO (final concentration: 90%) were added to the recovered cell solution, and the fluorescence intensity was measured. The results are illustrated in FIG. 8. P33-ICG1 and P34-ICG were taken up by the Colon 26 cells at a significantly high level as compared with PEG1, but at a lower level than that of ICG. Moreover, P34-ICG having a larger number of bound ICG and a higher rate of side chain hydrolysis was more taken up by the Colon 26 cells.

(Evaluation of Tumor Accumulation Property and Evaluation of Concentration in Blood)

Figure 9:
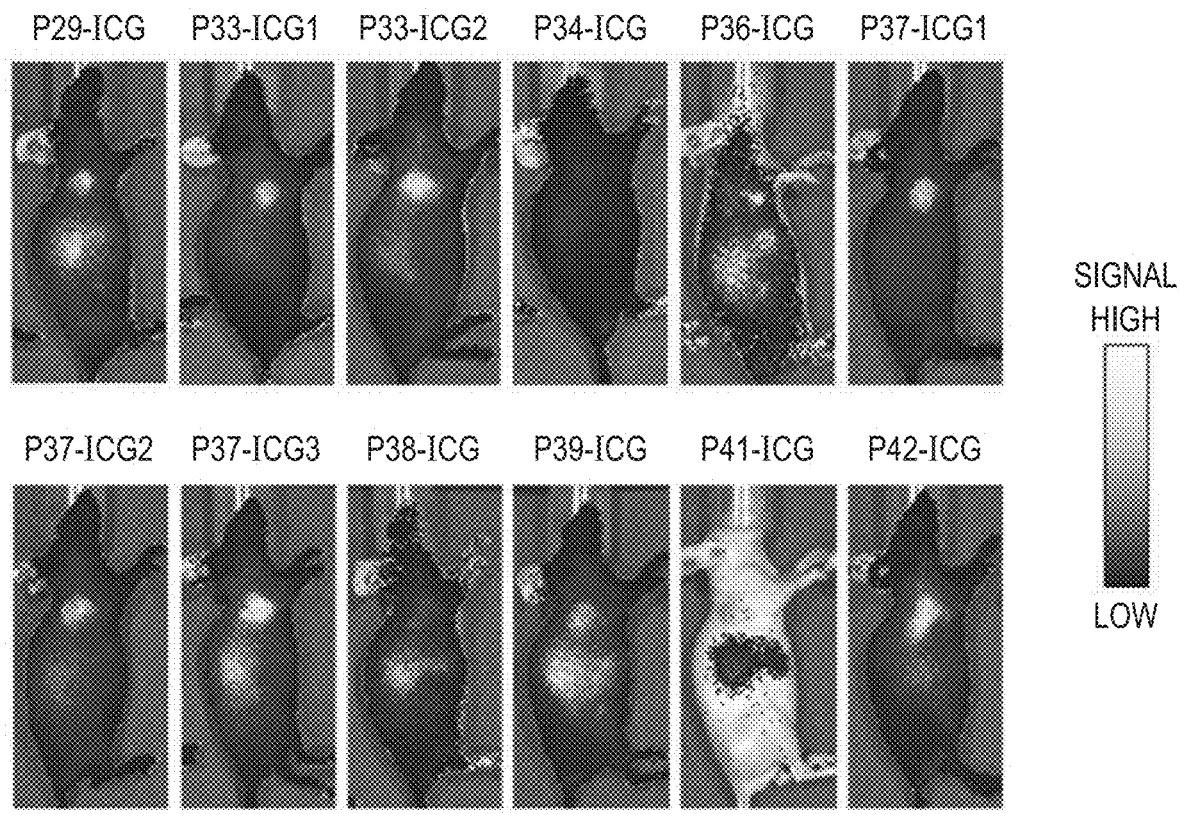
FIG. 9 illustrates a whole-body fluorescence image of a cancer-bearing mouse at 24 hours after administration of polymers in Examples of the present invention.

Each polymer (13 nmol) described in Table 9 was administered to the tumor bearing mouse provided by the above method, and fluorescence imaging of the tumor bearing mouse one day after administration was performed in the same manner as in the above method. FIG. 9 illustrates the result obtained by administering the polymer of the present invention to the tumor bearing mouse, and taking the whole-body fluorescence image after one day. The accumulation to a tumor was confirmed as to all of the polymers, and P33-ICG1, P33-ICG2, P37-ICG1, P37-ICG2, P37-ICG3 and P42-ICG had a high contrast to the neighborhood of the tumor. In addition, a tendency was found in which the fluorescence from the liver was stronger with an increase in the number of bound ICG. Furthermore, the amount of tumor accumulation and the amount of the dye in blood of the polymer of the present invention were quantitatively determined by the above method. The results are summarized in Table 9. A tendency was found in which the polymers having a high contrast to the neighborhood of the tumor in the whole-body fluorescence image of the mouse had a higher value of the amount of tumor accumulation. A tendency was found in which the tumor accumulation property was reduced with an increase in the rate of hydrolysis. In addition, the tumor/blood ratio was 2 or more for all of the polymers, and these polymers exhibited a significantly high tumor/blood ratio relative to PEG1 synthesized in Comparative Example 1. The significant test here was performed by the Student's t-test, and $P<0.05$ was determined as significant.

TABLE 9

| Polymer | Reaction dye | Amount of dye:amount of polymer during reaction | The number of bound dye per polymer molecule | Proportion of dye bonding unit | Amount of tumor accumulation (% ID/g) | Concentration in blood (% ID/g) | Tumor/blood ratio |
|---|---|---|---|---|---|---|---|
| P29-ICG | d1-1-1 | 16:1 | 5.4 | 2.1% | 3.7 ± 0.2 | 0.3 ± 0.0 | 11.3 ± 0.8 |
| P33-ICG1 | ICG-sulfo-OSu | 2:1 | 0.7 | 0.28% | 7.7 ± 0.2 | 2.1 ± 0.5 | 3.8 ± 0.9 |
| P33-ICG2 | d1-1-1 | 7:1 | 1.5 | 0.59% | 8.7 ± 1.2 | 0.9 ± 0.1 | 9.2 ± 2.0 |
| P34-ICG | ICG-sulfo-OSu | 2:1 | 1.9 | 0.75% | 1.6 ± 0.3 | 0.05 ± 0.01 | 30.5 ± 5.1 |

TABLE 9-continued

| Polymer | Reaction dye | Amount of dye:amount of polymer during reaction | The number of bound dye per polymer molecule | Proportion of dye bonding unit | Amount of tumor accumulation (% ID/g) | Concentration in blood (% ID/g) | Tumor/blood ratio |
|---|---|---|---|---|---|---|---|
| P36-ICG | d1-1-1 | 100:1 | 9.2 | 1.8% | 0.6 ± 0.0 | 0.1 ± 0.0 | 6.2 ± 1.1 |
| P37-ICG1 | d1-1-1 | 6:1 | 1.9 | 0.38% | 6.6 ± 1.9 | 1.8 ± 0.3 | 3.6 ± 0.5 |
| P37-ICG2 | d1-1-1 | 28:1 | 4.7 | 0.93% | 9.5 ± 1.4 | 2.0 ± 0.3 | 4.8 ± 1.2 |
| P37-ICG3 | d1-1-1 | 139:1 | 7.8 | 1.5% | 9.4 ± 0.6 | 1.5 ± 0.1 | 6.3 ± 1.0 |
| P38-ICG | d1-1-1 | 79:1 | 14.9 | 3.0% | 3.2 ± 0.2 | 0.2 ± 0.0 | 17.9 ± 0.1 |
| P39-ICG | d1-1-1 | 60:1 | 10.7 | 2.1% | 3.5 ± 0.6 | 0.2 ± 0.1 | 23.5 ± 7.8 |
| P41-ICG | d1-1-1 | 520:1 | 28.9 | 1.4% | 0.3 ± 0.0 | 0.1 ± 0.0 | 3.3 ± 0.1 |
| P42-ICG | d1-1-1 | 91:1 | 16.4 | 0.81% | 12.9 ± 0.6 | 6.4 ± 0.3 | 2.0 ± 0.2 |

Example 6: Photoacoustic Signal Measurement in Tumor Bearing Mouse Model (In Vivo Photoacoustic Tumor Imaging)

Figure 10:
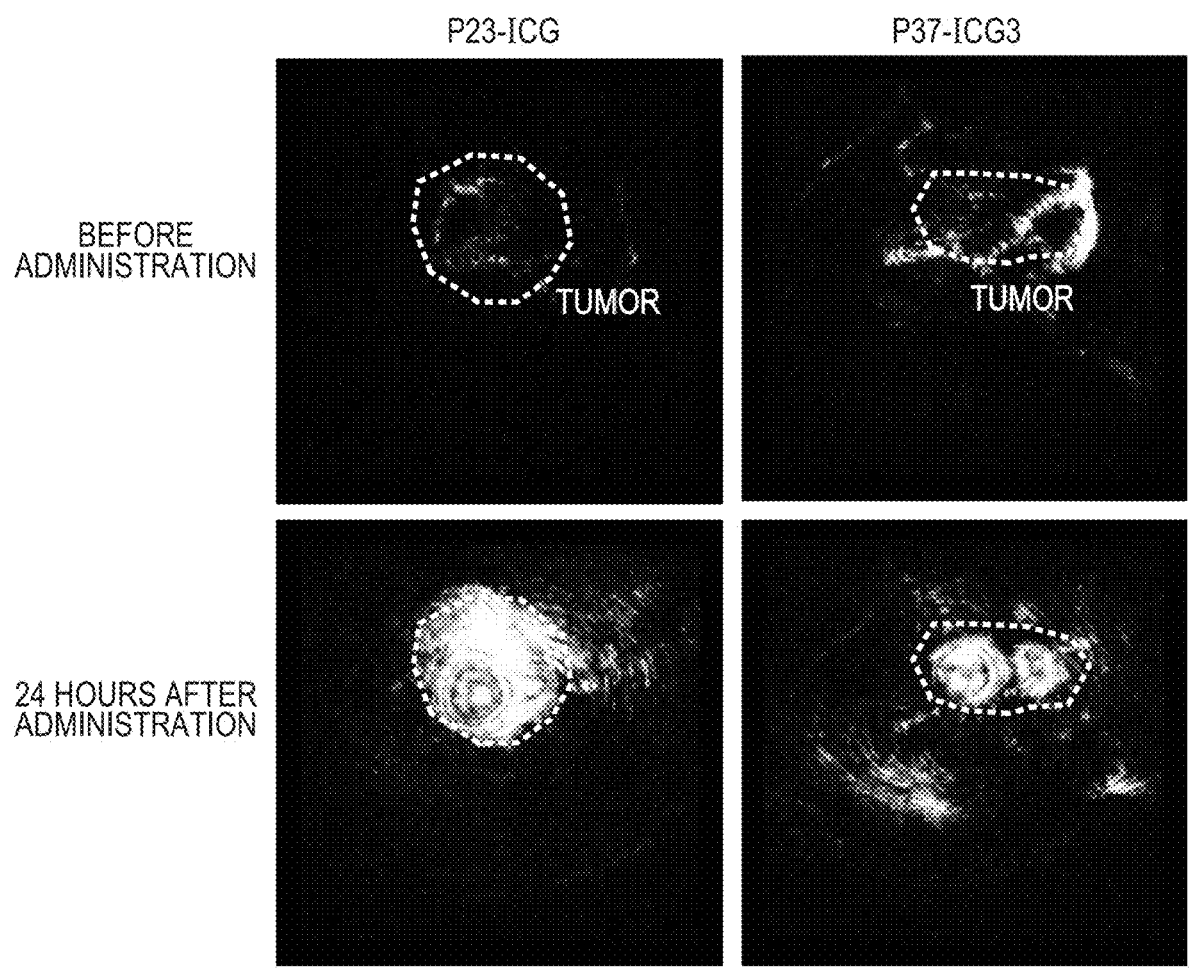
FIG. 10 illustrates an in vivo photoacoustic image of a cancer-bearing mouse at 24 hours after administration of polymers in Examples of the present invention.

In Examples of the present invention, the in vivo photoacoustic tumor imaging was performed using a photoacoustic imaging apparatus (Nexus128, produced by Endra Inc.). The cancer-bearing mouse prepared in the same manner as in the above evaluation of a tumor accumulation property was put to sleep under anesthesia and then fixed to the imaging apparatus. The photoacoustic signal was measured before administration of the polymer of the present invention P23-ICG or P37-ICG3 (each 52 nmol) and 24 hours after administration to obtain each three-dimensional reconstruction data. The photoacoustic signal image was drawn with OsiriX Imaging Software using the obtained three-dimensional reconstruction data (FIG. 10). The location and the shape of the tumor were clearly drawn in the tumor bearing mouse at 24 hours after administration of P23-ICG or P37-ICG3, indicating the usefulness of the polymer of the present invention as a photoacoustic tumor contrast agent.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-211915, filed Oct. 16, 2014 and Japanese Patent Application No. 2015-092782, filed Apr. 30, 2015 which are hereby incorporated by reference herein in their entirety.

The invention claimed is:

1. A polymer represented by formula (A1):

wherein in the formula (A1), $R_0$ represents a residue derived from a cationic polymerization initiator, or a functional group; $L_1$ represents a linker and $L_1$ may not be present; $D_1$ is represented by formula (d1-1); and $Z_1$ represents a structure comprising at least one unit represented by formula (A2), at least one unit represented by formula (A3), and at least one unit represented by formula (A4):

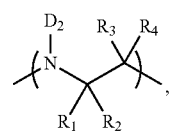

wherein in the formula (A2), $D_2$ is represented by the formula (d1-1); and $R_1$ to $R_4$ each independently represents a hydrogen atom, or a substituted or unsubstituted hydrocarbon group having 1 to 4 carbon atoms, in which, when a substituent is present, the substituent is a functional group including at least one selected from the group consisting of a halogen atom, an oxygen atom and a nitrogen atom;

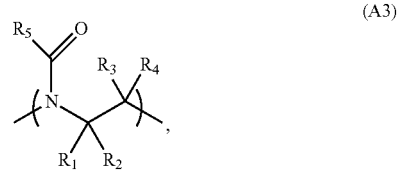

wherein in the formula (A3), $R_1$ to $R_4$ each independently represents a hydrogen atom, or a substituted or unsubstituted hydrocarbon group having 1 to 4 carbon atoms, in which, when a substituent is present, the substituent is a functional group including at least one selected from the group consisting of a halogen atom, an oxygen atom, and a nitrogen atom; and $R_5$ represents any of a methyl group, an ethyl group, an isopropyl group, a n-propyl group, a n-butyl group, a n-octyl group, a n-heptyl group, a phenyl group, a butenyl group, and a pentynyl group;

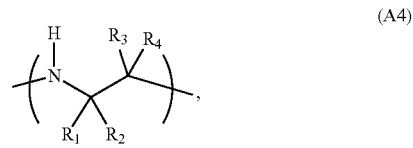

wherein in the formula (A4), $R_1$ to $R_4$ each independently represents a hydrogen atom, or a substituted or unsubstituted hydrocarbon group having 1 to 4 carbon atoms, in which, when a substituent is present, the substituent is a functional group including at least one selected from the group consisting of a halogen atom, an oxygen atom, and a nitrogen atom, and wherein a ratio of a unit represented by the formula (A4) to repeating units of the polymer is 12.6% or less as measured by electric conductivity:

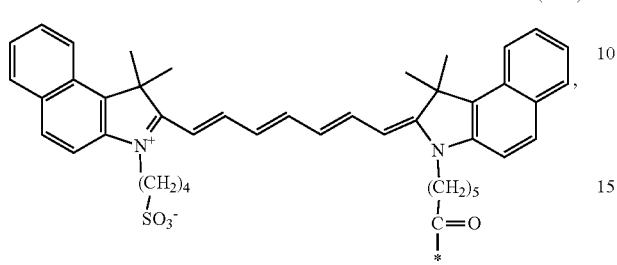
(d1-1)

wherein, in the formula (d1-1), * represents binding to $L_1$ in the formula (A1) or represents binding to $Z_1$ in the formula (A1) when $L_1$ is not present.

2. The polymer according to claim 1, wherein the polymer is a random copolymer having the unit represented by the formula (A2) and the unit represented by the formula (A3).

3. The polymer according to claim 1, wherein a ratio of the unit represented by the formula (A2) to repeating units carried by the polymer is 60% or less.

4. The polymer according to claim 1, wherein a ratio of the unit represented by the formula (A2) to repeating units carried by the polymer is 0.01% to 10%.

5. The polymer according to claim 1, wherein each of $R_1$ to $R_4$ is a hydrogen atom.

6. The polymer according to claim 1, wherein $L_1$ has a structure represented by any of formulas (l1) to (l14):

  (l1)

  (l2)

  (l3)

  (l4)

  (l5)

  (l6)

  (l7)

  (l8)

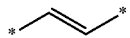  (l9)

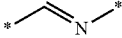  (l10)

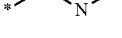  (l11)

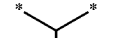  (l12)

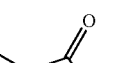  (l13)

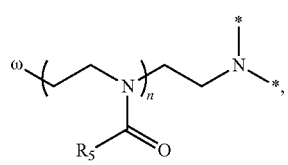  (l14)

wherein in the formulas (l1) to (l14), two * represent direct binding or indirect binding to $D_1$ and $Z_1$, respectively, in the formula (A1); and in the formula (l14), ω represents a residue derived from a terminal after completion of cationic polymerization reaction, or a functional group.

7. The polymer according to claim 1, wherein $R_5$ is an ethyl group.

8. The polymer according to claim 1, wherein a molecular weight of the polymer is 10000 to 200000, as measured by Gel Permeation Chromatography.

9. The polymer according to claim 1, wherein a molecular weight of the polymer is 10000 to 50000, as measured by Gel Permeation Chromatography.

10. The polymer according to claim 1, wherein $R_0$ is selected from a functional group derived from any of a dye, a reporter molecule, a target-binding molecule, and a polymer.

11. A contrast agent for photoacoustic imaging, comprising the polymer according to claim 1, and a dispersion medium.

12. The polymer according to claim 1, wherein $R_5$ is the isopropyl group.

13. The polymer according to claim 1, wherein a number of bound dye per polymer molecule is 1.9 to 7.8.

14. The polymer according to claim 13, wherein the number of bound dye per polymer molecule is 4.7 to 7.8.

* * * * *